US005635173A

United States Patent [19]
Warren et al.

[11] Patent Number: 5,635,173
[45] Date of Patent: Jun. 3, 1997

[54] INSECT REPELLENT AND ATTRACTANT COMPOSITIONS AND METHODS FOR USING SAME

[75] Inventors: Craig B. Warren, Rumson, N.J.; Jerry F. Butler, Gainesville, Fla.; Richard A. Wilson, Westfield, N.J.; Braja D. Mookherjee, Holmdel, N.J.; Leslie C. Smith, Plainsboro, N.J.; Anna B. Marin, Leonardo, N.J.

[73] Assignees: International Flavors & Fragrances, New York, N.Y.; The University of Florida, Gainesville, Fla.

[21] Appl. No.: 450,584

[22] Filed: May 25, 1995

Related U.S. Application Data

[62] Division of Ser. No. 241,555, May 12, 1994, which is a division of Ser. No. 130,256, Oct. 1, 1993, Pat. No. 5,401,500, which is a division of Ser. No. 948,142, Sep. 18, 1992, abandoned.

[51] Int. Cl.$^6$ .......................... A01N 27/00; A01N 25/08
[52] U.S. Cl. .................................... 424/84; 514/763
[58] Field of Search ........................ 424/84; 514/763, 514/919

[56] References Cited

U.S. PATENT DOCUMENTS 5,465,685 11/1995 Dotolo et al. ........................... 119/159

OTHER PUBLICATIONS

King, "Chemicals Evaluated as Insecticides and Repellents at Orlando, Fla.", U.S. Department of Agriculture, Agricultural Research Service, Agriculture Handbook No. 69 (published approximately 1951), (p. 218 specifically cited), (Item No. 6699: d–limonene).

Beroza and Green, I, "Materials Tested as Insect Attractants", Agricluture Handbook No. 239, Agricultural Research Service, U.S. Department of Agriculture, Issued Jun. 1963, pp. 112 and 114 specifically cited: Item Nos. 4612–4618: lavendin oil and lavender oil; and Item No. 4701: spike lavender oil).

Beroza and Green, II, "Materials Tested as Insect Attractants"; Agriculture Handbook No. 239, Agricultural Research Service, U.S. Department of Agriculture, Issued Jun. 1963, p. 11, Item No. 36 limonene.

Derwent Abstract 67–04579H, Abstracting JP 43–29014 (1968).

Derwent Abstract 91–099128, Abstracting JP 3–44305 (1991).

Primary Examiner—John Pak
Attorney, Agent, or Firm—Arthur L. Liberman

[57] ABSTRACT

Described is (i) a method of repelling *Musca domestica* L.(Diptera:Muscidae) or *Aedes aegyptae* for a finite period of time from a three-dimensional space inhabitable by *Musca domestica* L.(Diptera:Muscidae) or *Aedes aegyptae* consisting essentially of the step of exposing a three-dimensional space to an effective *Musca domestica* L.(Diptera:Muscidae) or *Aedes aegyptae*-repelling concentration and quantity of a geraniol-containing composition consisting essentially of 50–100% of geraniol with the remainder of the composition being a compound selected from the group consisting of citronellol and nerol and (ii) a method of attracting *Musca domestica* L.(Diptera:Muscidae) or *Aedes aegyptae* using lavender absolute, benzoin, dimethyl benzyl carbinyl acetate, jasmine absolute, racemic borneol, d-limonene and/or dihydrolinalool. The attractants taken alone or in combination find utility primarily as bait enhancers for acute toxins and/or trapping devices. The above-stated attractants and repellents are described to be useful as such or contained in a polymer which can be a biodegradable polymer such as compositions containing a major proportion of poly(epsilon caprolactone) homopolymers.

3 Claims, 14 Drawing Sheets

FIG.1
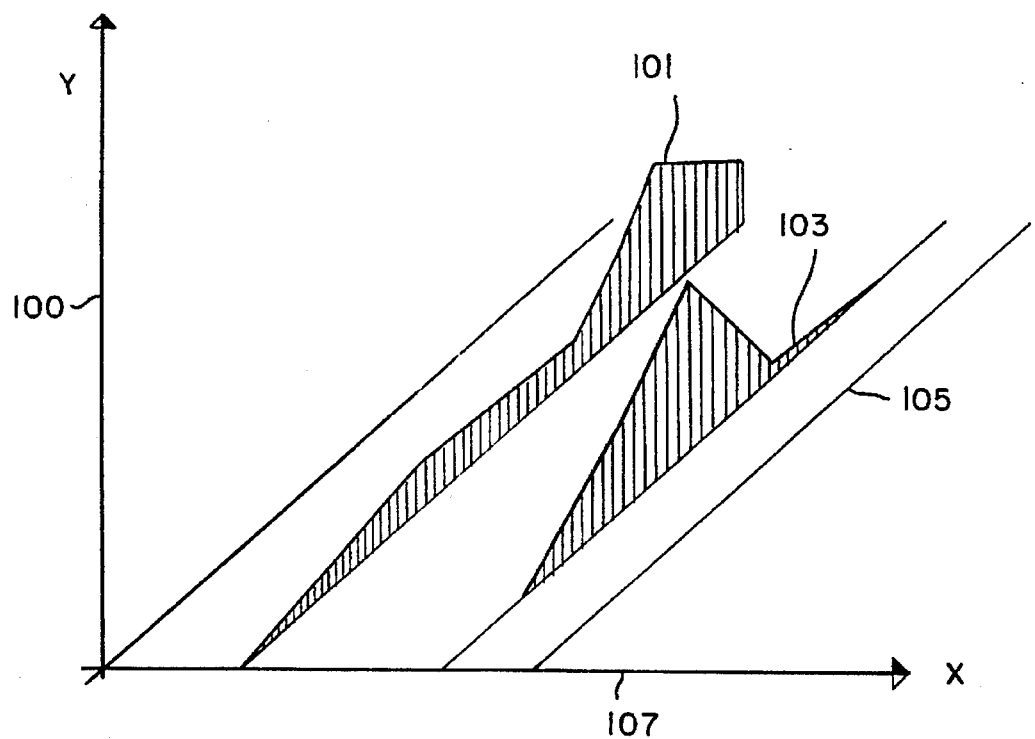
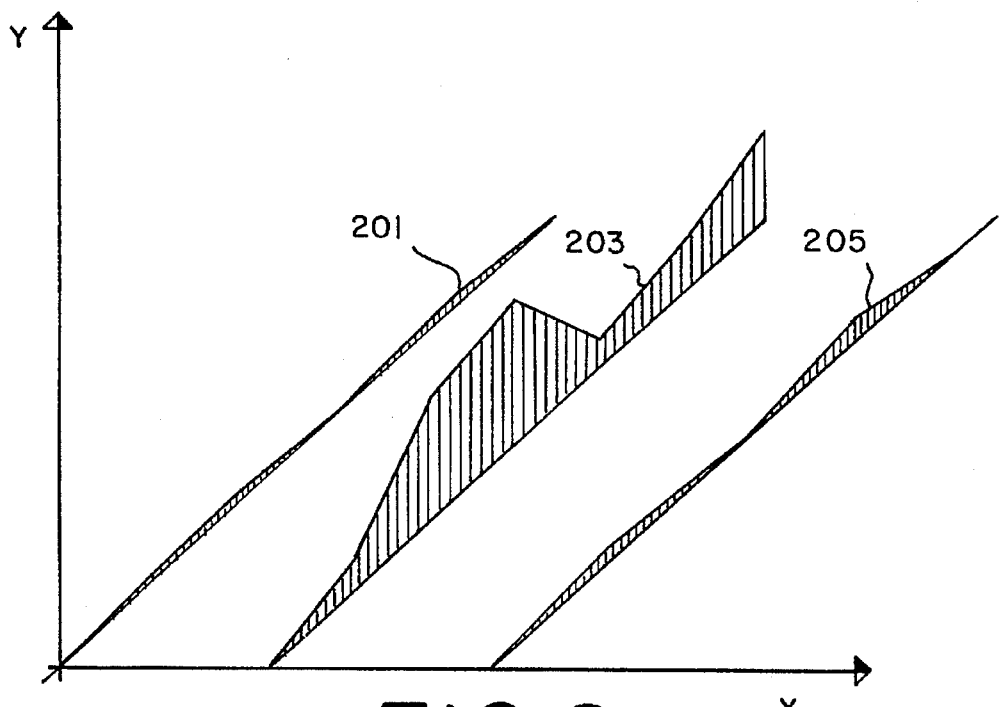
FIG.2

FIG.3
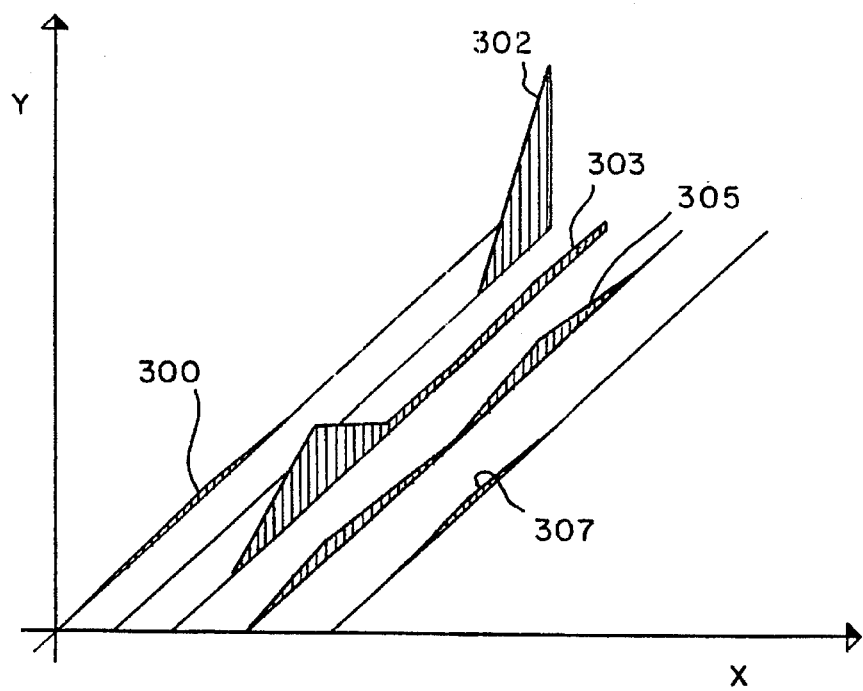
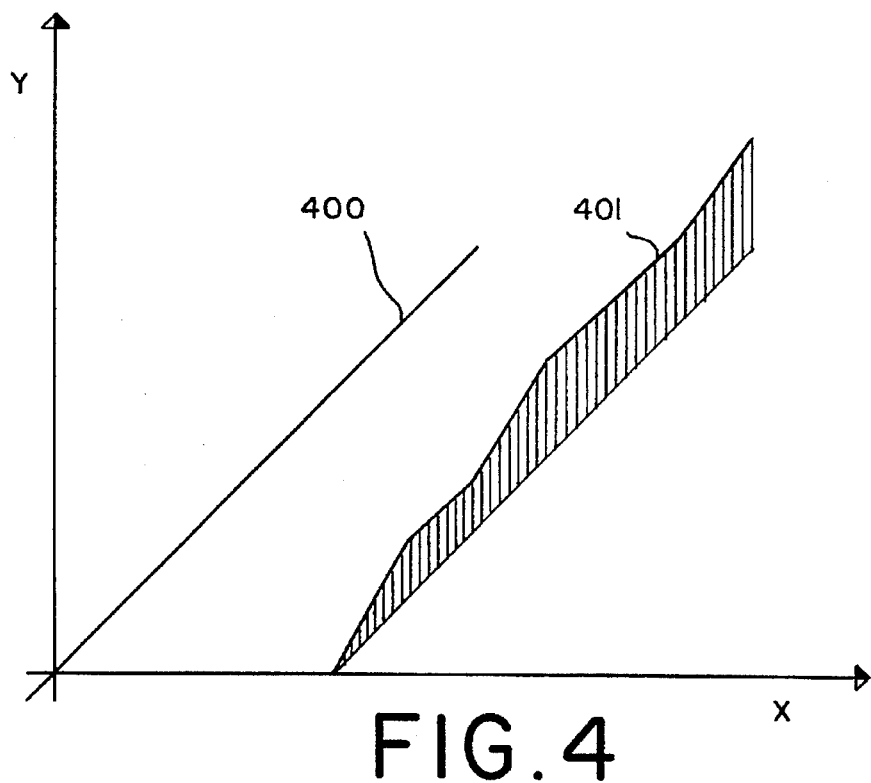
FIG.4

FIG.5-A
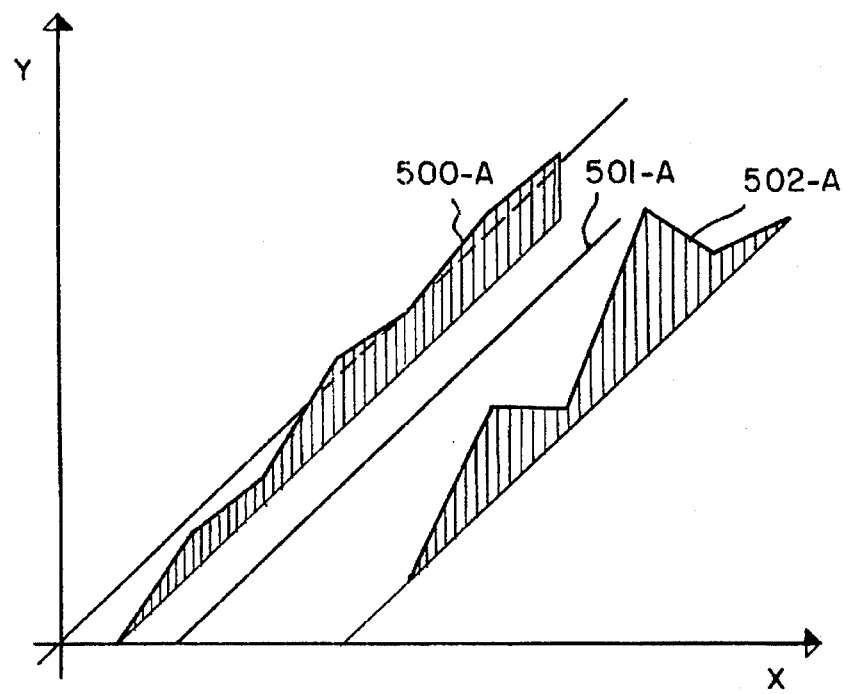
FIG.5-B
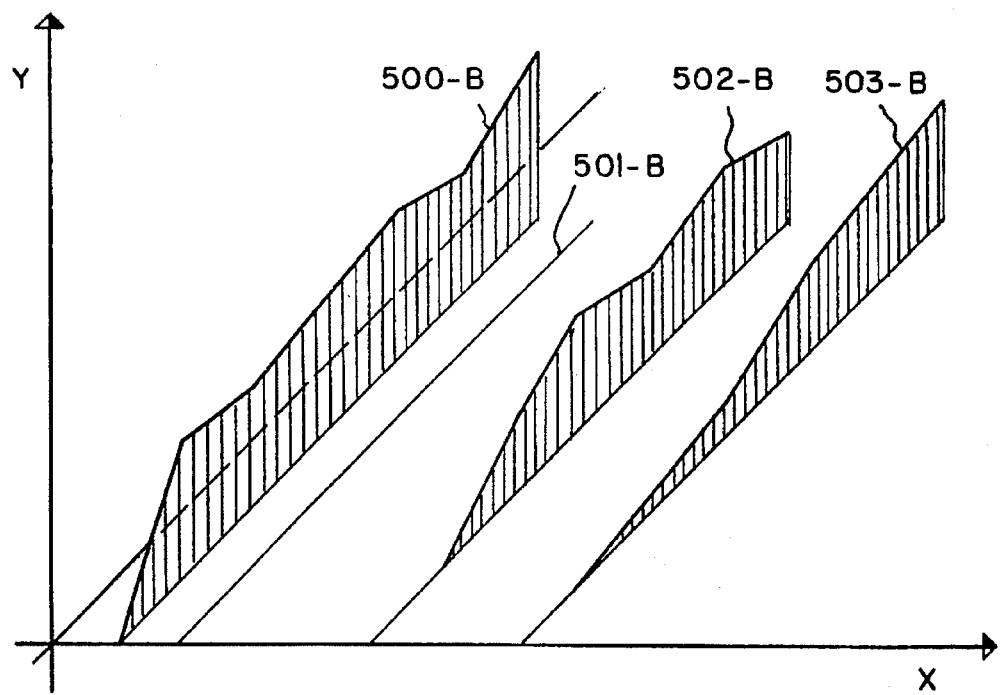

FIG.5-C
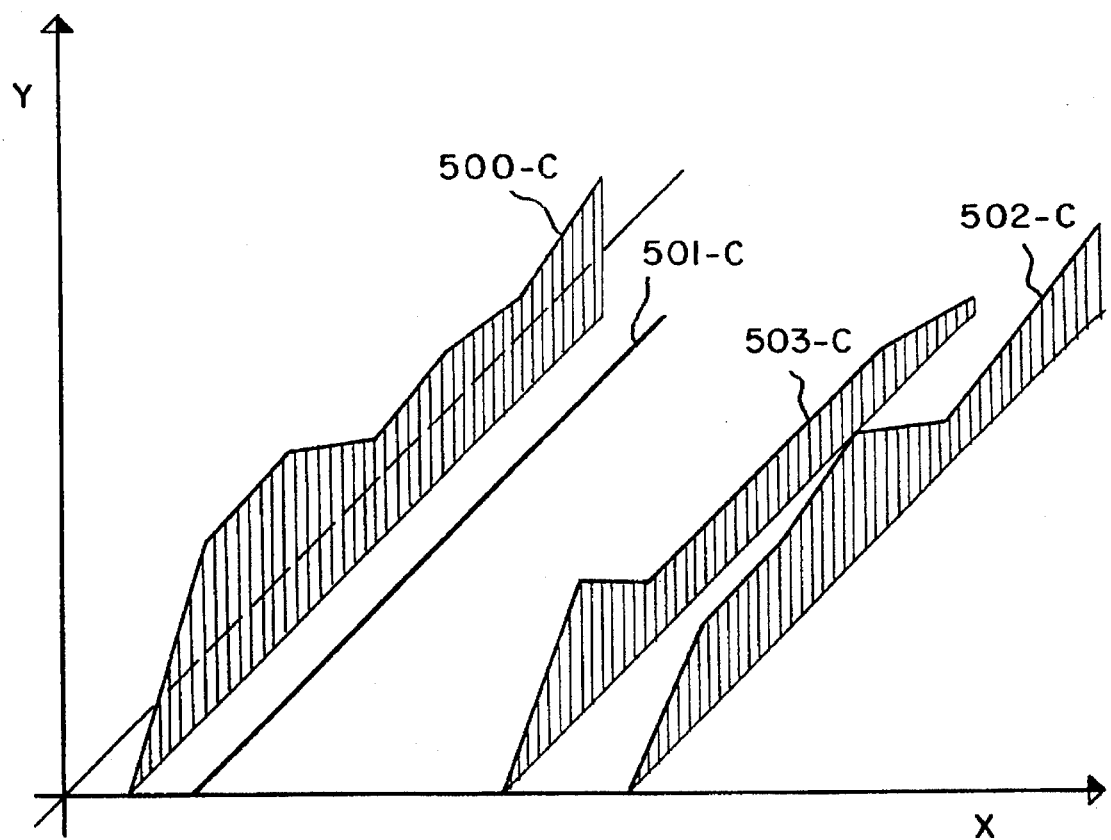

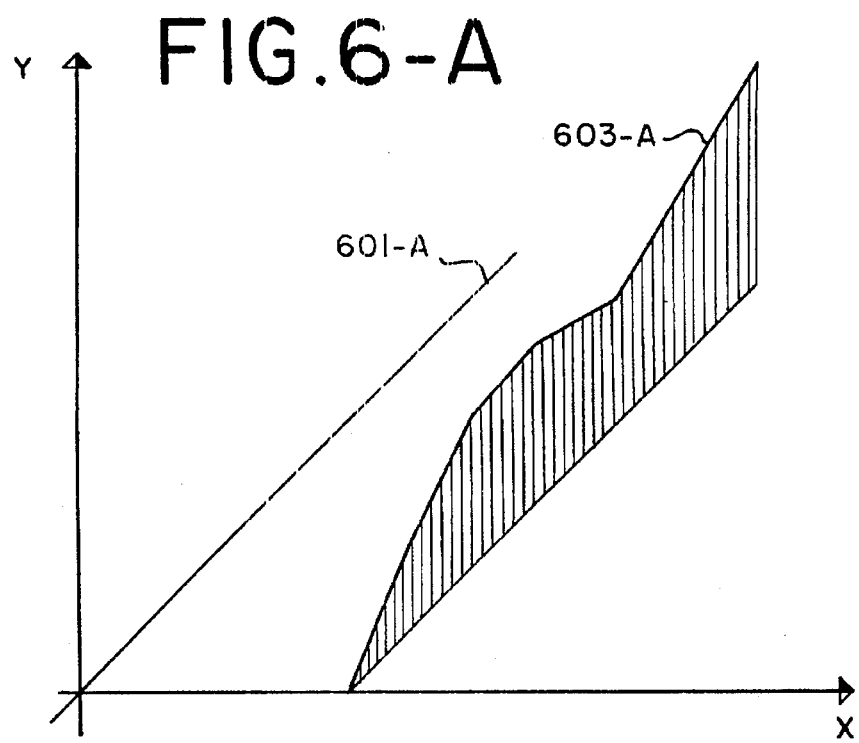
FIG.6-A
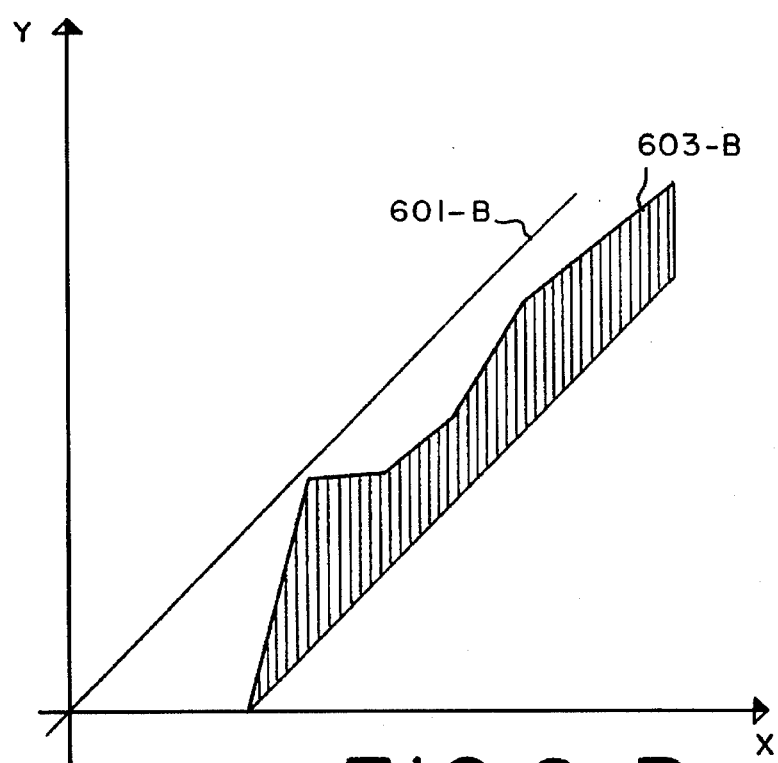
FIG.6-B

FIG.7-A
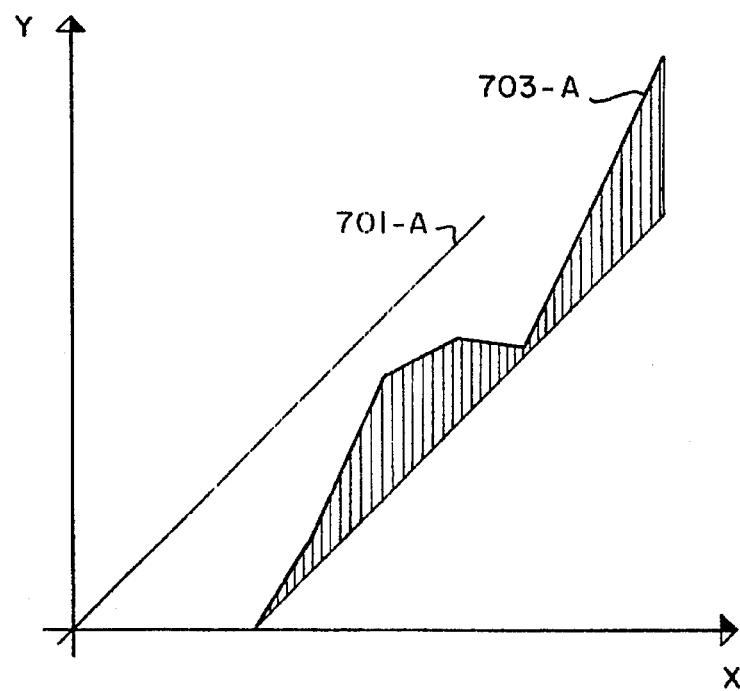
FIG.7-B
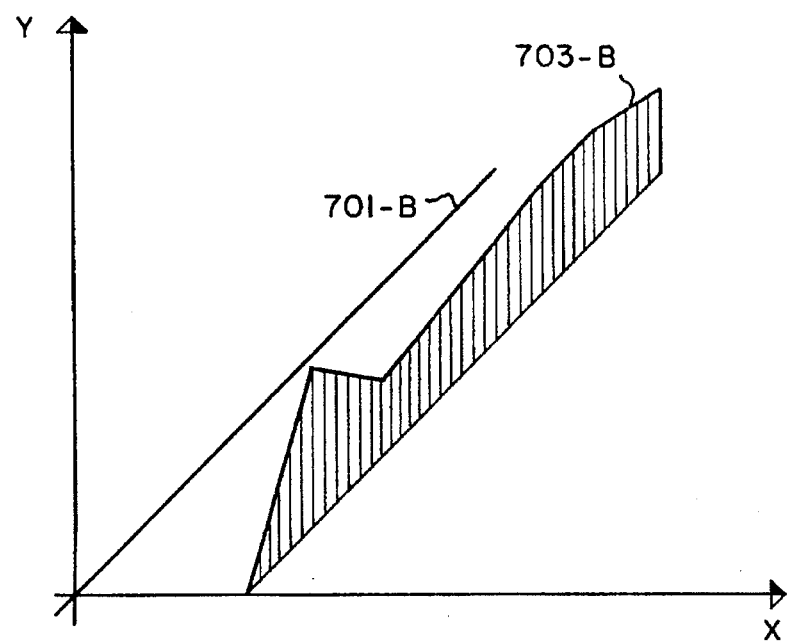

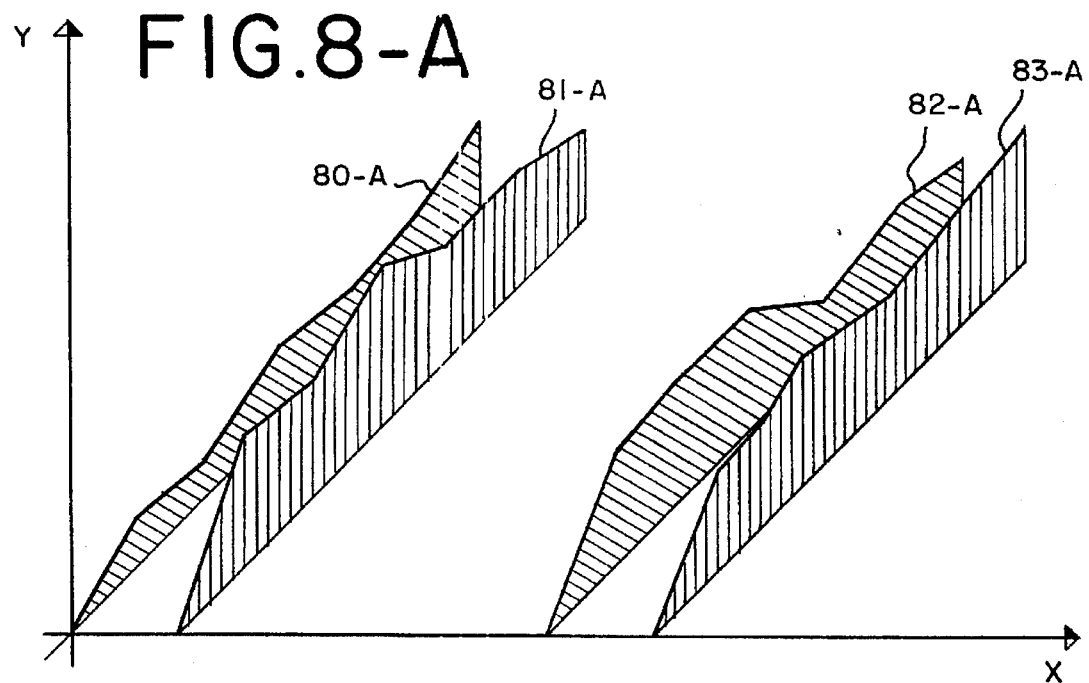
FIG.8-A
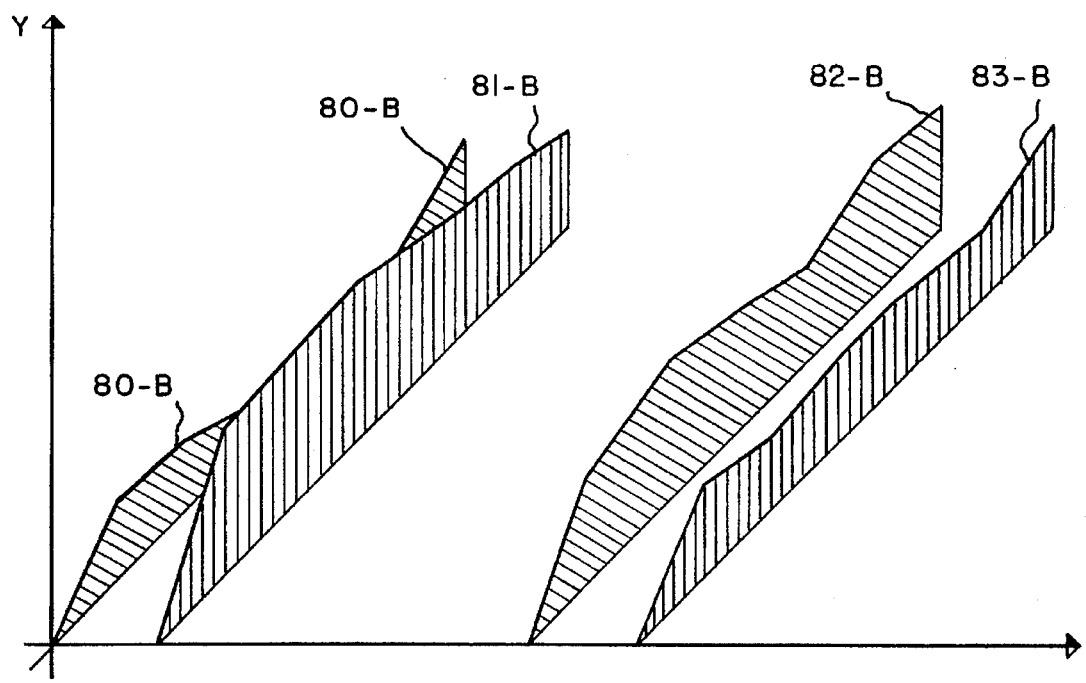
FIG.8-B

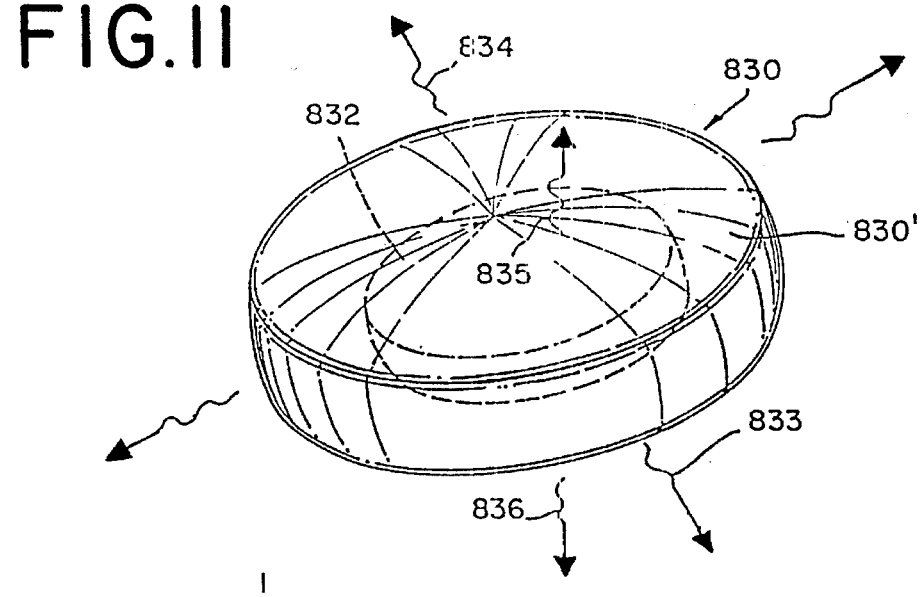
FIG.11
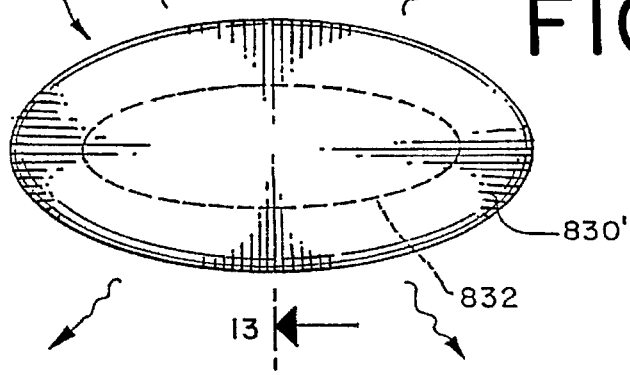
FIG.12
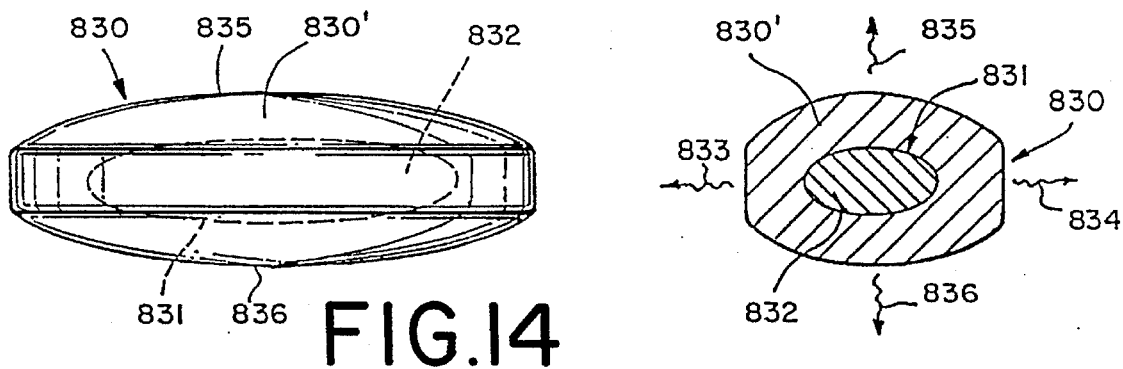
FIG.13
FIG.14

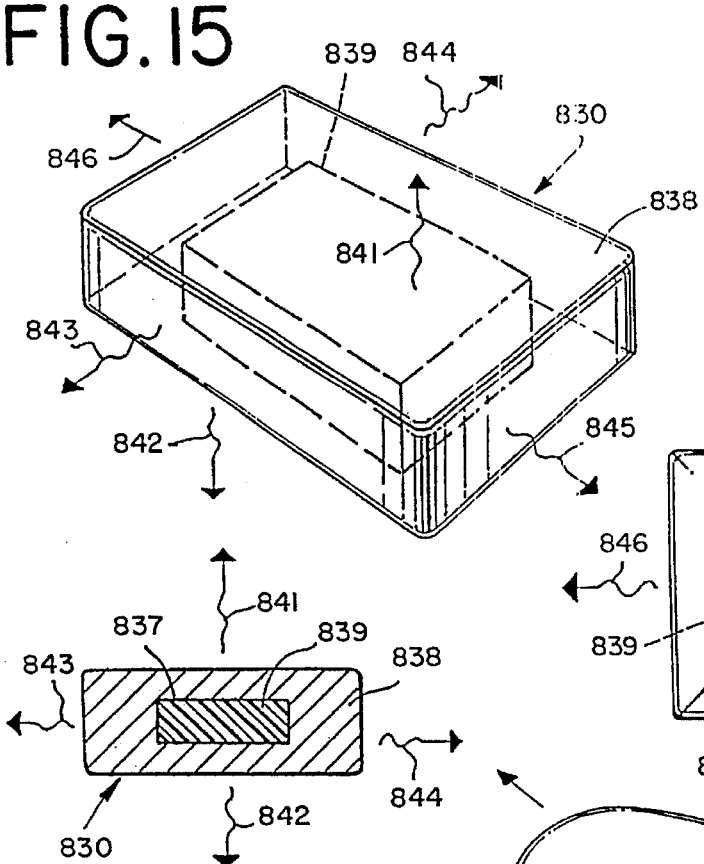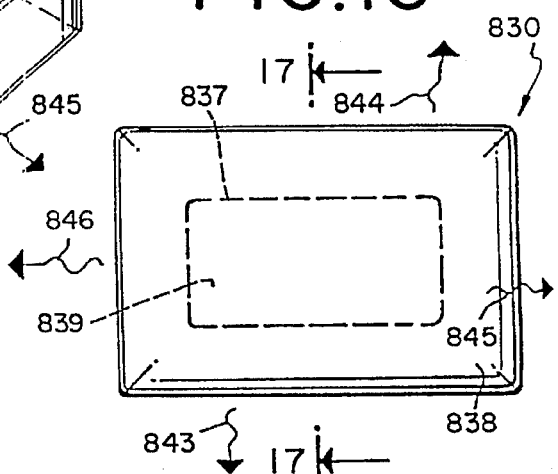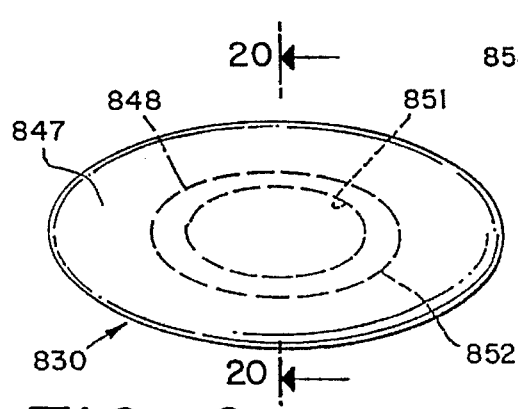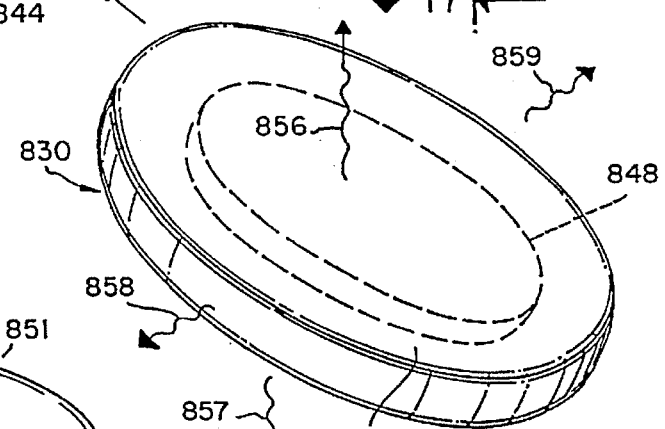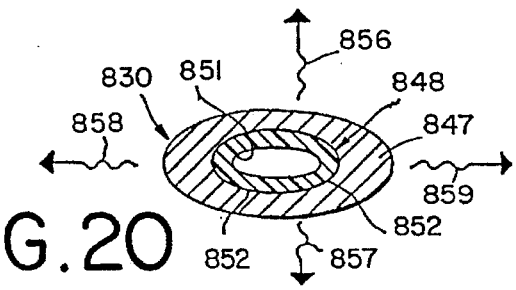

(1 HOUR)

(6 HOURS)

INSECT REPELLENT AND ATTRACTANT COMPOSITIONS AND METHODS FOR USING SAME

This is a divisional of application Ser. No. 08/241,555 filed on May 12, 1994; which, in turn, is a Streamline Divisional of Application for U.S. Letters Patent, Ser. No. 08/130,256 filed on Oct. 1, 1993; now U.S. Pat. No. 5,401,500 issued on Mar. 28, 1995; which, in turn, is a Streamline Divisional of U.S. Letters Patent, Ser. No. 07/948,142 filed on Sep. 18, 1992 (now abandoned) as originally filed.

BACKGROUND OF THE INVENTION

This invention relates to the use of geraniol-containing compositions consisting essentially of from 50–100% by weight of geraniol having the structure:

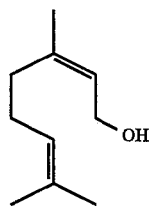

with the remainder of the composition being a compound selected from the group consisting of citronellol having the structure:

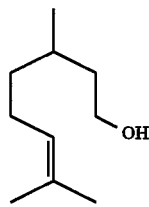

and nerol having the structure:

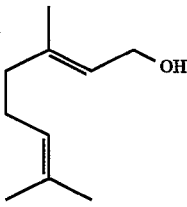

as repellents against house flies (*Musca domestica* L.(Diptera:Muscidae)) and mosquitoes (*Aedes aegyptae*).

This invention also relates to the use of the compounds:
lavender absolute;
bezoin having the structure:

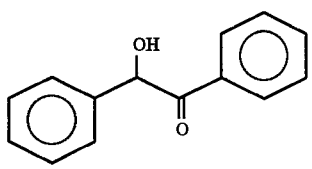

dimethyl benzyl carbinyl acetate having the structure:

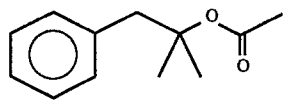

jasmine absolute;
racemic borneol having the structure:

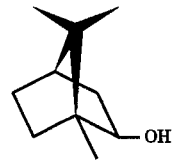

d-limonene having the structure:

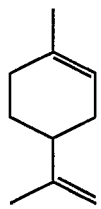

and dihydrolinalool having the structure:

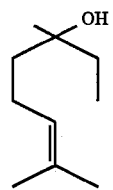

taken alone or taken together as attractants for house flies (*Musca domestica* L.(Diptera:Muscidae)) and mosquitoes (*Aedes aegyptae*).

This invention also relates to the use of such compounds and compositions of matter in insect repellents, soaps, insect traps and the like wherein, the compositions of matter are used as such or in combination in control release systems with polymers such as biodegradable polymers.

Unsaturated alcohols including 1-octen-4-ol and 1-nonen-3-ol are known with respect to controlling insects and 1-octen-4-ol and 1-nonen-3-ol are disclosed to be so useful in repelling *Musca domestica* L.(Diptera:Muscidae) and *Aedes aegyptae* in U.S. Pat. No. 4,764,367 issued on Aug. 16, 1988 and U.S. Pat. No. 5,118,711 issued on Jun. 2, 1992. Several unsaturated alcohols have been found to attract insects and others have been found to repel such insects. Thus, U.S. Pat. No. 4,152,442 issued on May 1, 1979 sets forth 6-nonen-1-ol in a composition of matter used as an attractant for the male Mediterranean fruit fly. Chem. Abstracts, Volume 103, No. 71086p concerns the synthesis of (Z)-8-dodecen-1-ol and its acetate as pheromone components of the Oriental Fruit Moth (*Grapholita molesta*). This is an abstract of the article in Acta Chem. Scan. Ser. B, 1985, B39(4), pages 267–72. U.S. Pat. No. 4,364,931 issued on Dec. 21, 1982 discloses the use of 9(Z)-tetradecen-1-ol acetate in attracting male white-line dart moths.

Chem. Abstracts, Volume 80, 1974, at No. 117098f discloses the use of trans-6-nonen-1-ol acetate as an ovipositional attractant and stimulant of the melon fly. U.S. Patent No. 2,254,665 issued on Sep. 1, 1941, on the other hand, discloses the use of aliphatic alcohols having from 10 to 14 carbon atoms to repel insects. Examples of the aliphatic alcohols of U.S. Pat. No. 2,254,665 are all saturated alcohols, to wit:

dodecyl alcohol;
octyl alcohol;
hexadecyl alcohol;
tetradecyl alcohol; and
undecyl alcohol.

U.S. Pat. No. 2,254,665 fails to disclose the use of unsaturated alcohols in insect repellent compositions.

Chem. Abstracts, Volume 74, 1974, at No. 99419f discloses various nonenyl acetates as attractants for female melon flies (abstract of J. Med. Chem. 1971, 14(3), pages 236–9) including trans-2-nonen-1-yl acetate.

On the other hand, Beroza, Materials Evaluated As Insecticides, Repellents and Chemosterilants at Orlando and Gainesville, Fla., 1952-1964. Agriculture Handbook No. 340, published by The Agricultural Research Service, U.S. Department of Agriculture, August, 1967 discloses the following items 5443–5452 as insect repellents (on a scale of 1-10) as follows:

Item 5443-3-phenyl-2-octen-1-ol repels the yellow fever mosquito from cloth at a level of "1" on a scale of 1-10.
Item 5444-2,6-dimethyl-4-octen-3-ol repels the yellow fever mosquito from cloth at a level of "1" on a scale of 1-10.
Item 5445-3,6-dimethyl-5-octen-3-ol repels the yellow fever mosquito from cloth at a level of "1" on a scale of 1-10.
Item 5446-3-6-dimethyl-5-octen-3-ol acetate repels the yellow fever mosquito from cloth at a level of "1" on a scale of 1-10.
Item 5447-2,7-dimethyl-5-octen-4-ol acetate repels the yellow fever mosquito from cloth at a level of "1" on a scale of 1-10.
Item 5448-3,7-dimethyl-6-octen-1-ol repels the yellow fever mosquito from cloth at a level of "2" on a scale of 1-10.
Item 5449-3,7-dimethyl-6-octen-1-ol carbanilate repels the yellow fever mosquito from cloth at a level of "1" on a scale of 1-10.
Item 5450-3,7-dimethyl-6-octen-2-ol repels the yellow fever mosquito from cloth at a level of "1" on a scale of 1-10.
Item 5451-3,6-dimethyl-6-octen-3-ol repels the yellow fever mosquito from cloth at a level of "1" on a scale of 1-10.
Item 5452-3,7-dimethyl-6-octen-3-ol repels the yellow fever mosquito from cloth at a level of "2" on a scale of 1-10.
Beroza, Agriculture Handbook No. 340 at Item 7977 indicates that undecyl alcohol acetate has insect repelling properties as follows:

Yellow fever mosquito: "1" on a scale of 1-10 Tick at a level of "2" on a scale of 1-10. European Published Patent Application 478,846 (abstracted at Chem. Abstracts, Volume 116:250531v discloses the use of borneol as an "environmentally friendly" ant repellent. U.S. Pat. No. 4,774,081 issued Sep. 27, 1988 and corresponding European Application 275,085 discloses as an example of a contact insect repellent against cockroaches and other crawling insects, citronellol, geraniol, nerol and butyl hydroxy anisole and mixtures thereof (column 2, lines 31–39). Chem. Abstracts, Volume 105:204742q discloses that compounds from the leaves of bay (*Laurus nobills L.*) are useful repellents for Tribolium castaneum (Herbst) and these compounds include, inter alia, geraniol when present at 50 ppm. Chem. Abstracts, Volume 113:110945w (abstract of Japan Kokai Tokkyo Koho 02/67202) discloses that, inter alia, linalool, geraniol, citronellol and nerol are repellent when incorporated into porous inorganic microcapsules against cockroaches, slugs, ants, etc.. Chem. Abstracts, Volume 104:30390k discloses the repellency against house flies of citronellol.

However, attractancy of geraniol towards certain insect genuses is disclosed in "Handbook of Insect Pheromones and Sex Attractants" Mayer et al CRC Press, 1991 at pages 708, 709, 866 and 867.

Biodegradable polymers containing insect repellents including polymers containing at least a major proportion of poly(epsilon caprolactone) homopolymers are disclosed by Munteanu, et al, in U.S. Pat. No. 4,496,467 issued on Jan. 29, 1985, U.S. Pat. No. 4,469,613 issued on Sep. 4, 1984 and U.S. Pat. No. 4,548,764 issued on Oct. 22, 1985.

Referring back to Beroza, Materials Evaluated As Insecticides, Repellents And Chemosterilants at Orlando and Gainesville, Fla., 1952-1964 (cited, supra) Beroza discloses that the compound having the structure:

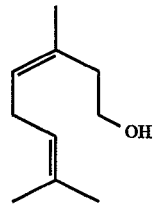

taken in admixture with the compound having the structure:

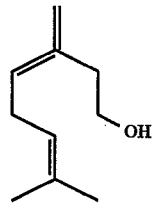

have repellency against the yellow fever mosquito on cloth at a level of "2" on a scale of 1-10.

PCT Application 91/15118 published on Oct. 17, 1991 (Beldock, et al) alleges the use of a mixture of geraniol in combination with terpineol, citronella and rhodenol extract as repellent against ticks and biting flies including mosquitoes and black flies. It is alleged in PCT Application 91/15118 that the composition of matter TREO® containing:

| | |
|---|---|
| 0.06% | terpineol; |
| 0.05% | citronella; |
| 0.08% | rhodenol extract; and |
| 0.06% | geraniol | is such a useful insect repellent composition.

Prior art published prior to the invention followed by reduction to practice of the invention of the instant patent application does not teach applicants' invention.

BRIEF DESCRIPTION OF THE DRAWINGS

FIG. 1 is a series of graphs depicted in three dimensions (in a rectangular mode for the "X" and "Y" axes) showing the relative attractiveness or repellency of air, lavender absolute and a mixture of geraniol, citronellol and nerol containing 61.49 mole percent geraniol having the structure:

Figure 9:
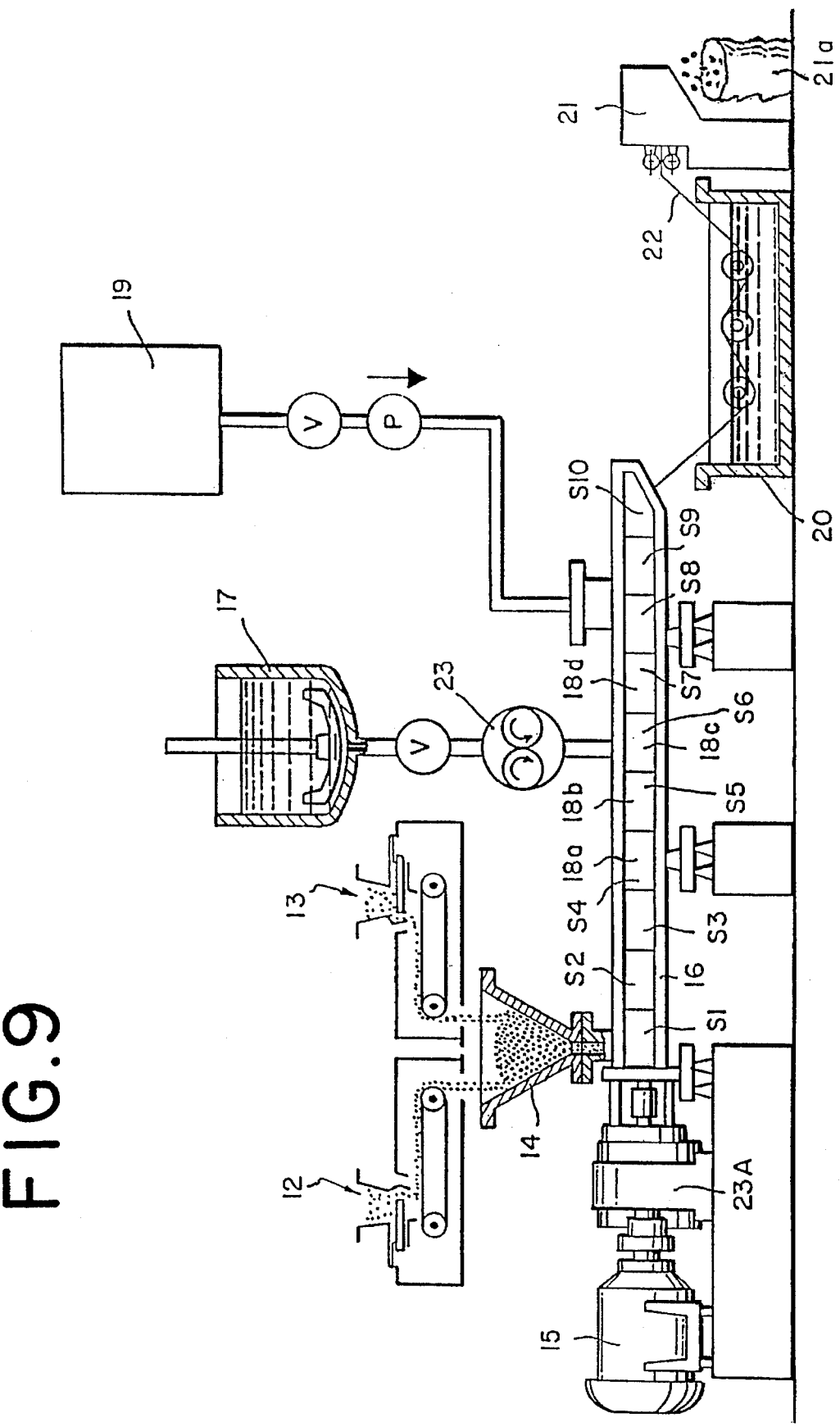

13.98 mole percent nerol having the structure:

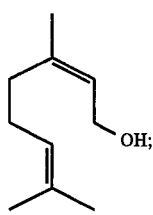

and 24.53 mole percent citronellol having the structure:

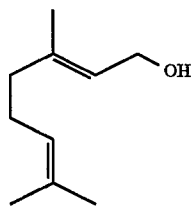

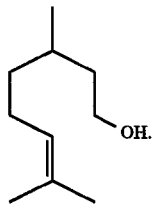

The graphs are based on experiments run for a period of six hours with six intervals of one hour each using as the insect to be tested the mosquito (*Aedes aegyptae*). The results are tabulated in Table I, infra.

FIG. 2 is a series of graphs depicted in three dimensions (in a rectangular mode for the "X" and "Y" axes) showing the relative attractiveness or repellency of benzoin having the structure:

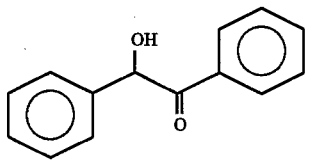

and a mixture of 61.49 mole percent geraniol; 13.98 mole percent nerol and 24.53 mole percent citronellol. The graphs are based on experiments run for a period of six hours with six intervals of one hour each using as the insect to be tested the house fly *Musca domestica L.*(Diptera:Muscidae). The results are tabulated in Table II, infra.

FIG. 3 is a series of graphs depicted in three dimensions (in a rectangular mode for the "X" and "Y" axes) showing the relative attractiveness or repellency of tridecene nitrile, air, jasmine absolute, dimethyl benzyl carbinyl acetate having the structure:

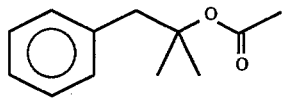

and a mixture containing 81.28 mole percent geraniol and 18.72 mole percent of a mixture of nerol and citronellol with the mole ratio of citronellol:nerol being 1.78. The graphs are based on experiments run for a period of six hours with six intervals of one hour each using as the insect to be tested the house fly, *Musca domestica L.*(Diptera:Muscidae). The results are tabulated in Table III, infra.

FIG. 4 is a series of graphs depicted in three dimensions (in a rectangular mode for the "X" and "Y" axes) showing the relative attractiveness and repellency of air and a mixture containing 61.49 mole percent geraniol, 13.98 mole percent nerol and 24.53 mole percent citronellol. The graphs are based on experiments run for a period of twelve hours with six intervals of two hours each using as the insect to be tested the mosquito (*Aedes aegyptae*). The results are tabulated in Table IV, infra.

FIG. 5A is a series of graphs depicted in three dimensions (in a rectangular mode for the "X" and "Y" axes) showing the relative attractiveness or repellency of borneol having the structure:

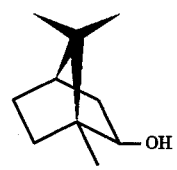

(racemic borneol), d-limonene having the structure:

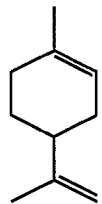

and a mixture of 61.49 mole percent geraniol, 13.98 mole percent nerol and 24.53 mole percent citronellol. The graphs are based on experiments run for a period of one hour with six intervals of 10 minutes each using as the insect to be tested the mosquito, (*Aedes aegyptae*). The results are tabulated in Table V(A), infra.

FIG. 5B is a series of graphs depicted in three dimensions (in a rectangular mode for the "X" and "Y" axes) showing the relative attractiveness or repellency for racemic borneol, d-limonene, air and a mixture of 61.49 mole percent geraniol, 13.98 mole percent nerol and 24.53 mole percent citronellol. The graphs are based on experiments run for a period of six hours with six intervals of one hour each using as the insect to be tested the mosquito (*Aedes aegyptae*). The results are tabulated in Table V(B), infra.

FIG. 5C is a series of graphs depicted in three dimensions (in a rectangular mode for the "X" and "Y" axes) showing the relative attractiveness or repellency of air, d-limonene, racemic borneol and a mixture of 61.49 percent geraniol, 13.98 percent nerol and 24.53 percent citronellol. The graphs are based on experiments run for a period of twelve hours with six intervals of two hours each using as the insect to be tested the mosquito (*Aedes aegyptae*). The results are tabulated in Table V(C), infra.

FIG. 6A is a series of graphs depicted in three dimensions (in a rectangular mode for the "X" and "Y" axes) showing the relative attractiveness or repellency of air and a mixture of 61.49 mole percent geraniol, 13.98 mole percent nerol and 24.53 mole percent citronellol. The graphs are based on experiments run for a period of one hour with six intervals of ten minutes each using as the insect to be tested the mosquito (*Aedes aegyptae*). The results are tabulated in Table VI(A), infra.

FIG. 6B is a series of graphs depicted in three dimensions (in a rectangular mode for the "X" and "Y" axes) showing the relative attractiveness or repellency of air and a mixture of 61.49 mole percent geraniol, 13.98 mole percent nerol and 24.53 mole percent citronellol. The graphs are based on experiments run for a period of six hours with six intervals of one hour each using as the insect to be tested the mosquito (*Aedes aegyptae*). The results are tabulated in Table VI(B), infra.

FIG. 7A is a series of graphs depicted in three dimensions (in a rectangular mode for the "X" and "Y" axes) showing the relative attractiveness and repellency of air and a mixture of 61.49 mole percent geraniol, 13.98 mole percent nerol and 24.53 mole percent citronellol. The graphs are based on experiments run for a period of one hour with six intervals of ten minutes each using as the insect to be tested the mosquito (*Aedes aegyptae*). The results are tabulated in Table VII(A), infra.

FIG. 7B is a series of graphs depicted in three dimensions (in a rectangular mode for the "X" and "Y" axes) showing the relative attractiveness and repellency of air and a mixture of 61.49 mole percent geraniol, 13.98 mole percent nerol and 24.53 mole percent citronellol. The graphs are based on experiments run for a period of six hours with six intervals of one hour each using as the insect to be tested the mosquito (*Aedes aegyptae*). The results are tabulated in Table VII(B), infra.

FIG. 8A is a series of graphs depicted in three dimensions (in a rectangular mode for the "X" and "Y" axes) showing the relative attractiveness or repellency of benzaldehyde, air, dihydrolinalool having the structure:

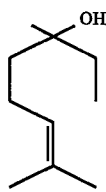

and the composition of matter TREO® (a trademark of Primavera Products Inc. of Northvale, N.J. TREO® is indicated to contain the following ingredients:

Octyl methoxycinnamate;
Benzophenone-3;
Octyl salicylate;
Water;
Glycerin;
Octylpalmitate;
PVP/Eicosene Copolymer;
Stearic Acid;
Cetyl Phosphate;
DEA Cetyl Phosphate;
Steapyrinium Chloride;
Cetyl Alcohol;
Dimethicone;
Glyceryl Stearate;
Imidazolidinyl Urea;
Methylparaben;
Propylparaben;

Butylated Hydroxy Anisole having the structure:

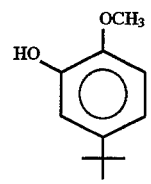

and a complicated mixture of perfumery materials including:
D-Limonene;
Phenylethyl alcohol;
Cis-Hexenyl Acetate;
Alpha-Terpineol;
Benzyl Acetate;
Citronellol;
Geraniol;
Cyclamal;

4-Methoxy-2-ethylhexyl cinnamate having the structure:

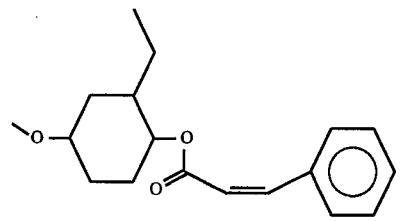

Uvinol M-40 having the structure:

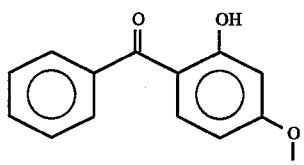

Cyclamal having the structure:

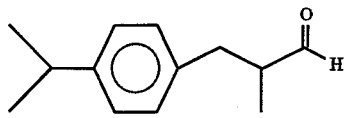

Lilial having the structure:

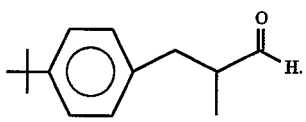

The graphs are based on experiments run for a period of one hour with six intervals of ten minutes each using as the insect to be tested the mosquito (*Aedes aegyptae*). The results are tabulated in Table VIII(A), infra.

FIG. 8B is a series of graphs depicted in three dimensions (in a rectangular mode for the "X" and "Y" axes) showing the relative attractiveness or repellency of benzaldehyde, dihydrolinalool, air and TREO®. The graphs are based on experiments run for a period of six hours with six intervals of one hour each using as the insect to be tested the mosquito (*Aedes aegyptae*). The results are tabulated in Table VIII(B), infra.

FIG. 9 is a cut-away side elevation schematic diagram of a screw extruder during the compounding of a resin with insect attractants or repellents including either the geraniol composition useful in our invention or one or more of the attractants, to wit:

Lavender absolute;
Benzoin;
Dimethyl benzyl carbinyl acetate;
Jasmine absolute;
Racemic borneol;
d-Limonene; and/or
Dihydro linalool while simultaneously adding foaming agent into the hollow portion of the barrel of the extruder and incorporates the pelletizing apparatus used in the pelletizing of the extruded foamed tow product produced as a result of the extrusion operation.

Figure 10:
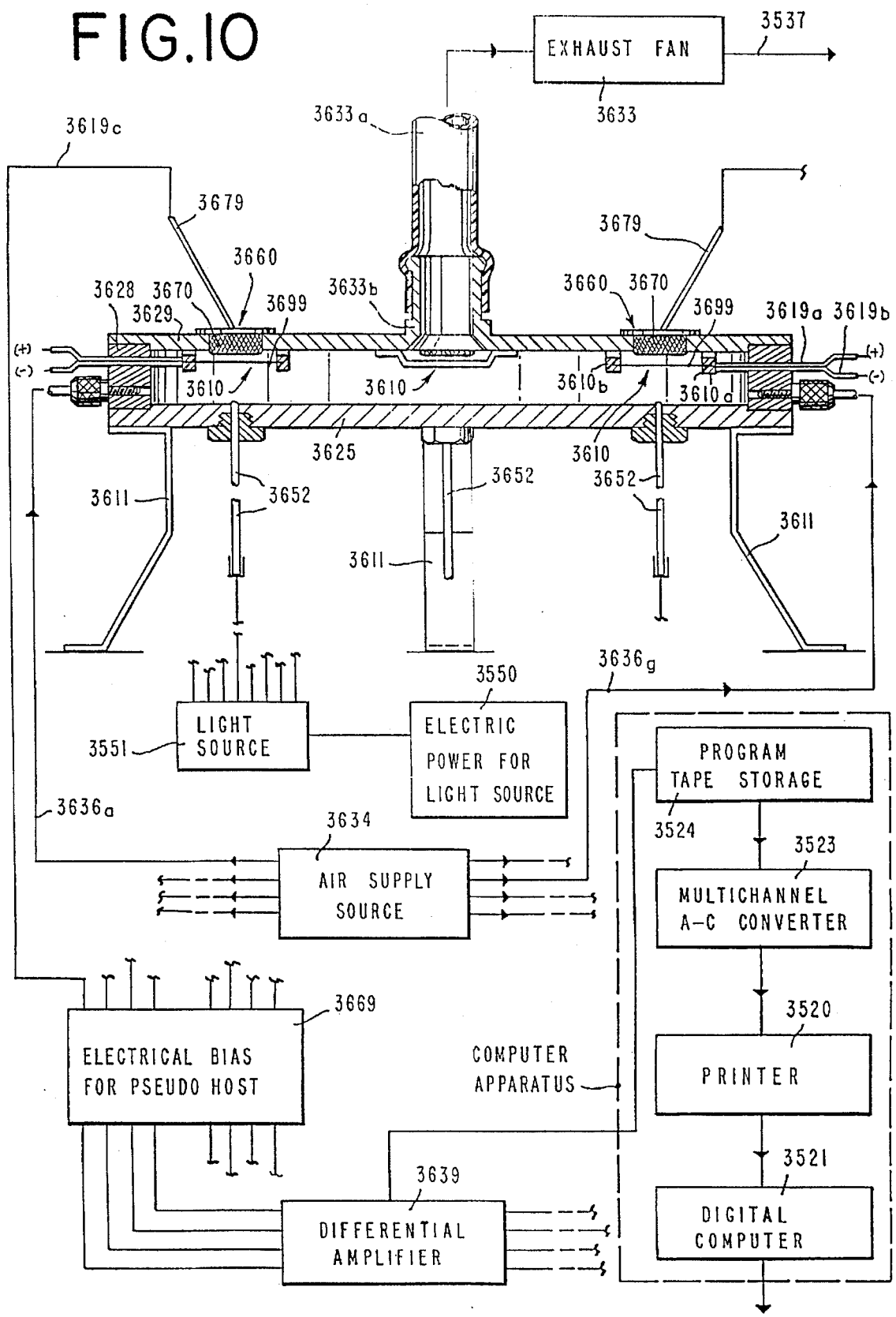

FIG. 10 is a cut-away side elevation view of the base section of the olfactometer apparatus used in carrying out the testing of the attractants or repellents of our invention indicating in schematic block flow diagram form the utilization of computer-assisted efficacy measuring apparatus; but showing only an air supply entry into the side ports of the olfactometer apparatus with the treatment agent being contained in a control release matrix upstream from the air supply source.

FIG. 11 is a perspective view of an ellipsoidally shaped detergent tablet containing a solid core which includes fused foamed polymeric particles which contain insect repellents which are one of the geraniol-containing compositions of our invention and, if desired, also containing an additional polymer, e.g., polyethylene. The polymer particles may, if desired, also contain additional aromatizing agents.

FIG. 12 is the top view of the ellipsoidally-shaped detergent Table X of FIG. 11.

FIG. 13 is a cut-away front view of the ellipsoidally-shaped detergent Table X of FIG. 11 in the direction of the arrows in FIG. 12.

FIG. 14 is a side-view of the ellipsoidally-shaped detergent Tablet X of FIG. 11.

FIG. 15 is a perspective view of a rectangular parallelepiped-shaped detergent tablet containing a rectangular parallelepiped-shaped core comprising a major proportion of fused foamed polymeric particles which contain insect repellents (e.g., one of the geraniol-containing compositions of our invention) and may or may not be aromatized and, if desired, an additional polymer which may or may not contain insect repellent compositions and which may or may not be aromatized.

FIG. 16 is a top view of the rectangular parallelepiped-shaped detergent tablet of FIG. 15.

FIG. 17 is a cut-away front view of the rectangular parallelepiped-shaped tablet of FIG. 15 looking in the direction of the arrows in FIG. 16.

FIG. 18 is a perspective view of an ellipsoidally-shaped detergent tablet containing a hollow insect repellent agent (and if desired an aromatizing agent) containing core which includes fused foamed polymeric particles containing insect repellent and if desired aromatizing agent or, in the alternative, a hollow core of fused foamed polymer wherein the insect repellent (and if desired the aroma imparting agent) is in the solid polymer and not in the void of the plastic core.

FIG. 19 is a top view of the ellipsoidally-shaped detergent tablet of FIG. 18.

FIG. 20 is a front cut-away view of the ellipsoidally-shaped detergent tablet of FIG. 18 looking in the direction of the arrows in FIG. 19, the core thereof being hollow and either containing an insect repellent material (and if desired an aroma imparting liquid) or in the alternative being a hollow core wherein the insect repellent material (and if desired the aroma imparting material) is in the solid fused foamed polymeric particles which make up the core and wherein the void does not contain anything.

Figure 21:
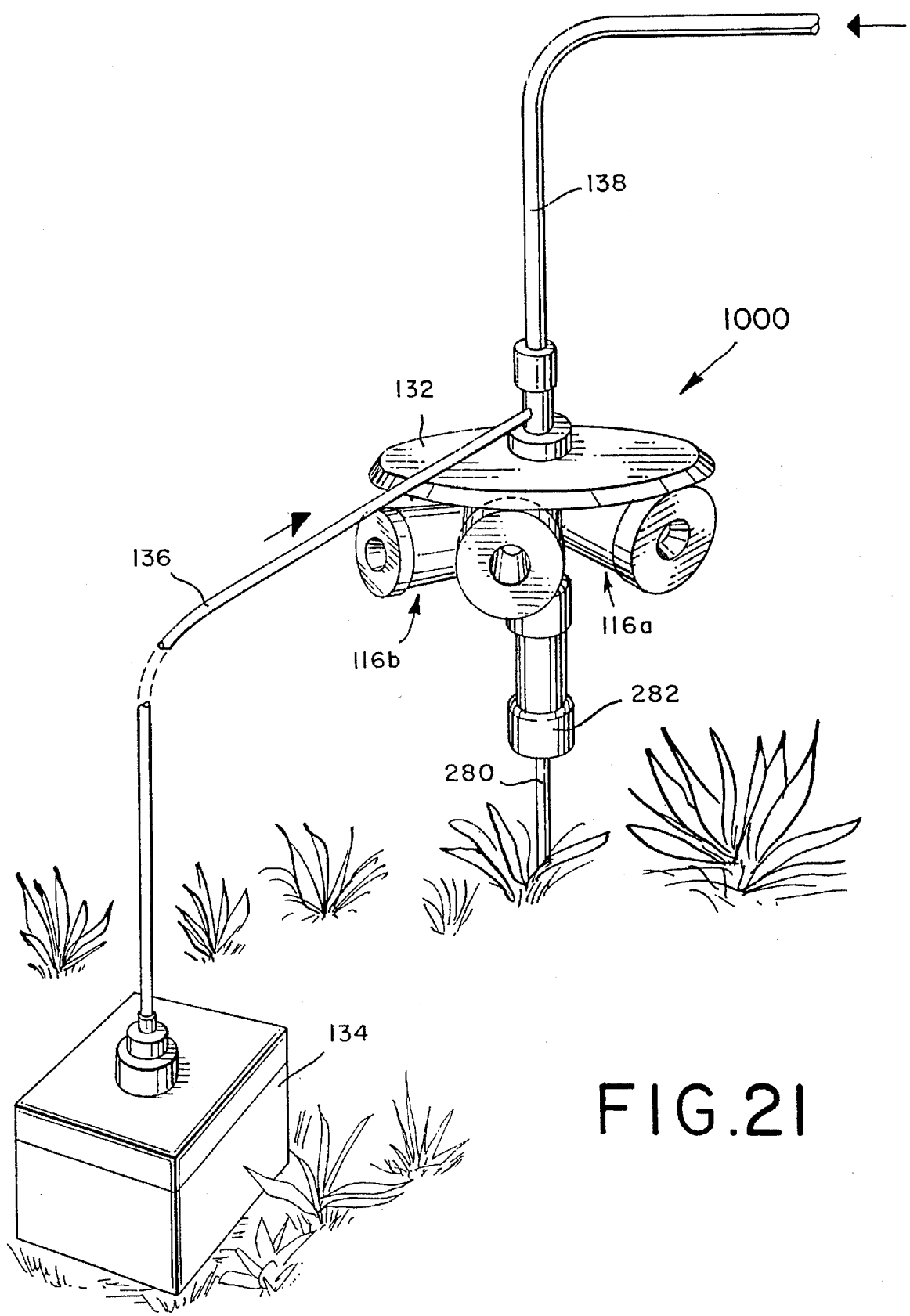

FIG. 21 is a perspective view of the semiochemical field trap for testing the attractiveness or repellency for blood feeding arthropods using the geraniol-containing repellency composition of our invention or the attractants of our invention which may be either:

Lavender absolute;
Benzoin;
Dimethyl benzyl carbinyl acetate;
Jasmine absolute;
Racemic borneol;
d-Limonene; and/or
Dyhydro Linalool.

The semiochemical field trap is described in detail in Application for U.S. Letters Patent, Ser. No. 887,138 filed on May 22, 1992 the specification for which is incorporated herein by reference.

Figure 22:
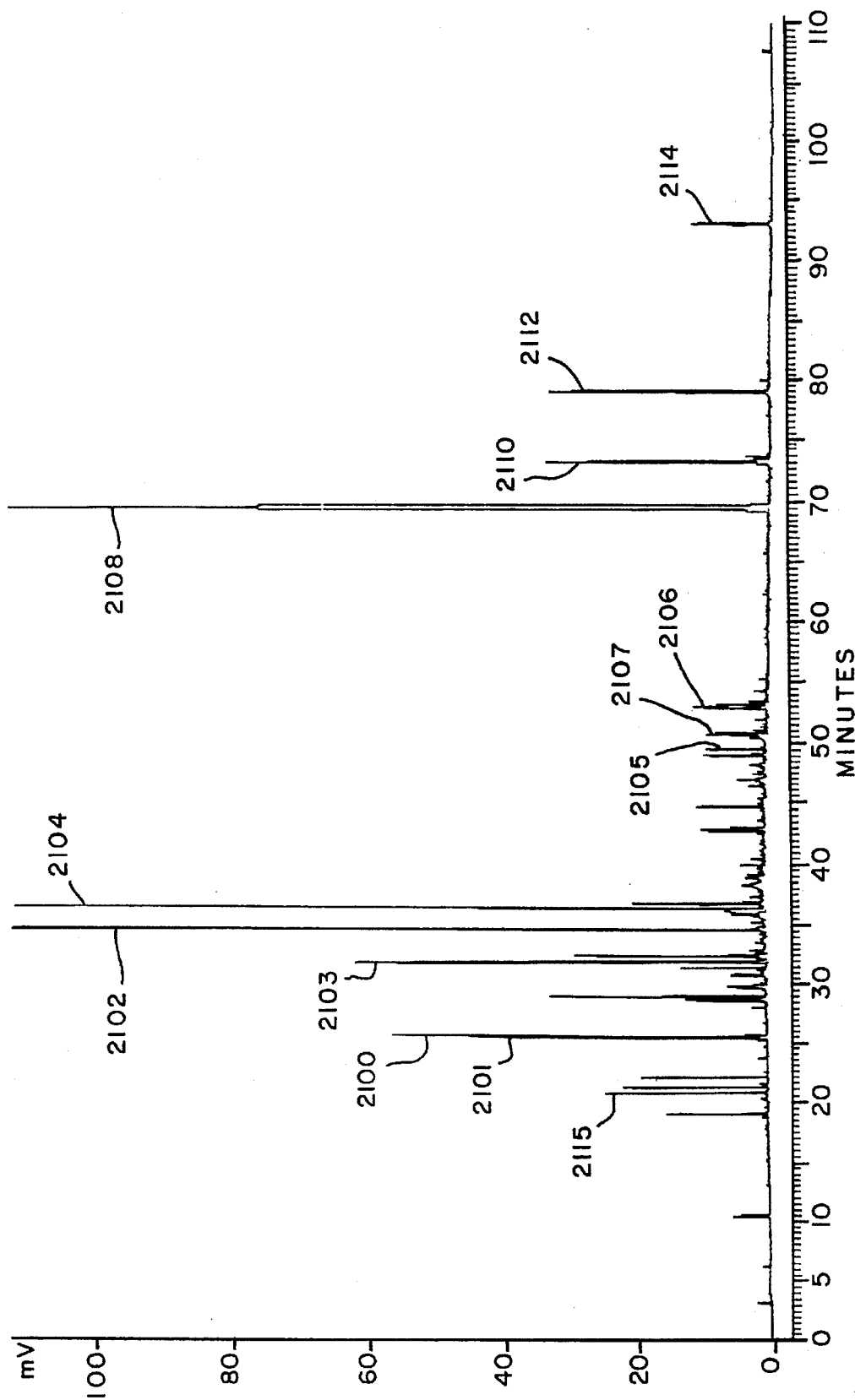

FIG. 22 is the GC-Mass spectrum for a market sample of TREO® marketed by Primavera Products, Inc. of Northvale, N.J. (conditions: 50 meter×0.32 mm FS-OV-1 column programmed from 50° C.–225° C. at 2° C. per minute).

Figure 23:
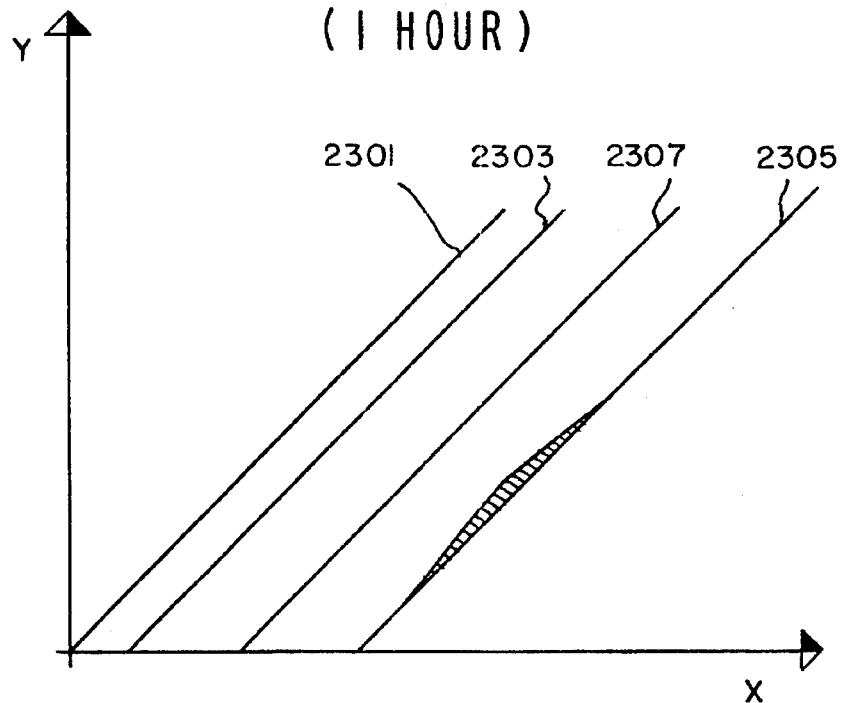

FIG. 23 is a series of graphs depicted in three-dimensions (in a rectangular mode for the "X" and "Y" axes) showing the relative attractiveness or repellency of various compositions of matter for mosquitoes (*Aedes aegyptae*) of the materials:

(i) mixture containing 61.54 mole percent geraniol, 24.5 mole percent citronellol and 13.98 mole percent nerol;

(ii) mixture containing 98.95 mole percent geraniol and 1.05 mole percent nerol;

(iii) mixture containing 81.8 mole percent geraniol, 11.66 mole percent citronellol; and 6.53 mole percent nerol; and (iv) air.

The graphs are based on experiments run for a total of one hour with six intervals of ten minutes each. The results are tabulated in Table IX(A), infra.

Figure 24:
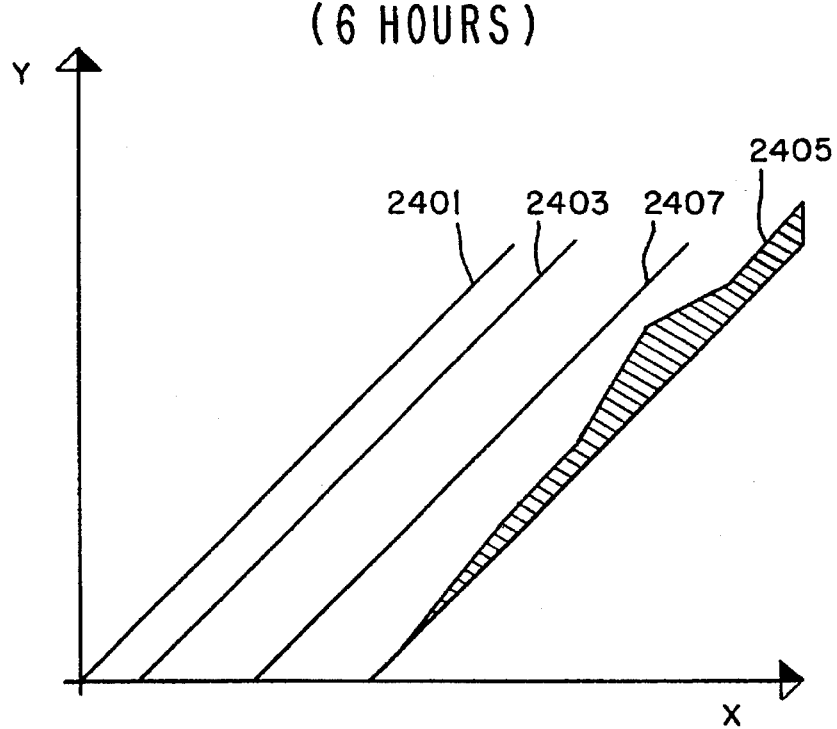

FIG. 24 is a series of graphs depicted in three dimensions (in a rectangular mode for the "X" and "Y" axes) showing the relative attractiveness or repellency for mosquitoes (Aedes aegyptae) of the following compositions of matter:

(i) mixture of 61.54 mole percent geraniol, 24.5 mole percent citronellol and 13.98 mole percent nerol;

(ii) mixture of 98.95 mole percent geraniol and 1.05 mole percent nerol;

(iii) mixture of 81.8 mole percent geraniol, 11.66 mole percent citronellol and 6.53 mole percent nerol; and (iv) air.

The graphs are based on experiments run for a total of six hours with six intervals of one hour each. The results are tabulated in Table IX(B), infra.

SUMMARY OF THE INVENTION

This invention relates to the use of geraniol-containing compositions which contain 50–100% by weight geraniol having the structure:

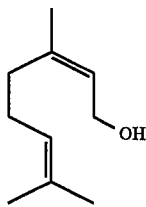

and the remainder of the composition being a compound selected from the group consisting of citronellol having the structure:

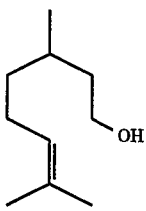

and nerol having the structure:

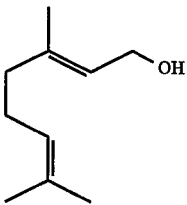

as insect repellents against house flies (*Musca domestica* L.(Diptera:Muscidae)) and mosquitoes (*Aedes aegyptae*).

This invention also relates to the use of one or more of the materials:

Lavender absolute, Benzoin having the structure:

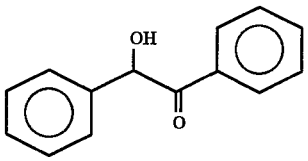

Dimethyl benzyl carbinyl acetate having the structure:

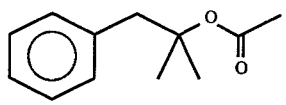

Jasmine absolute;
Racemic borneol having the structure:

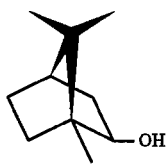

d-limonene having the structure:

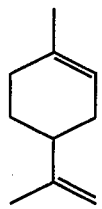

and/or
Dihydro linalool having the structure:

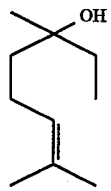

as attractants for house flies (*Musca domestica* L.(Diptera:Muscidae)) and mosquitoes (*Aedes aegyptae*).

Our invention also relates to the use of the foregoing insect repellent compositions in personal soap compositions, for example, the insect repellent soap composition described in U.S. Pat. No. 4,707,496 issued on Nov. 17, 1987, the specification for which is incorporated by reference herein. Thus, in applying the teachings of U.S. Pat. No. 4,707,496 to our invention, a topical insect repellent soap composition and a method of protection using such a composition is described where the insect repellent soap composition comprises:

(i) from 63.0 up to 99.5% by weight of a soap mixture containing from 4.1 to 7% by weight of a soap of caprylic acid, from 3.8 to 7% of a soap of capric acid, from 32.1 to 45% of a soap of lauric acid, from 12 to 17.5% by weight of a soap of myristic acid, from 5.0 up to 10% by weight of a soap of palmitic acid, from 1.6% to 3% by weight of a soap of stearic acid, from 3.5 to 5% by weight of a soap of oleic acid and from 0.9 to 5% by weight of a soap of linoleic acid;

(ii) from 0.1 up to 2% by weight of $C_8$-$C_{18}$ is straight chain fatty acids.

(iii) from 10 up to 30% by weight of one of the geraniol-containing compositions of our invention as set forth, supra, and (iv) from 0.2 up to 5% by weight of an effective residual insecticide as described in U.S. Pat. No. 4,707,496.

Other insect repellent soaps can be produced by adding a geraniol-containing composition of our invention to one or more of the compositions described and claimed in U.S. Pat. No. 4,453,909 issued on Jun. 12, 1984 and U.S. Pat. No. 4,438,010 the specifications for which are incorporated by reference herein. Described in said U.S. Pat. No. 4,453,909 and U.S. Pat. No. 4,438,010 is a process for making a tablet of saop containing a perfume containing core, hollow or solid fabricated from a hard plastic material either thermo-setting or thermoplastic. The soap from the resulting composite tablet is useable until the core is washed clean and contains functional ingredients, e.g., the repellents described, supra, and optionally, aromatizing agent until the core is washed clean. This obviates the wastage of soap which normally occurs as a conventional soap tablet becomes very thin on use and at the same time gives rise to a continuously functional ingredient containing soap, (e.g., repellent and optionally aromatizing agent) tablet. Thus, this invention also relates to detergent bars having a plastic core containing a geraniol-containing composition and optionally, a perfume. More particularly, this invention relates to detergent bars intended for conventional toilet soap uses either as hand soaps or bath or shower soaps which are elastic or inelastic in nature but which contain a solid plastic core containing insect repellent and optionally perfume giving them unique properties which alleviate wastage thereof and causes the environment surrounding the soap on use thereof to be both insect repellent and optionally aromatized in an aesthetically pleasing manner.

Yet another aspect of our invention relates to the use of the geraniol-containing repellents of our invention taken further in combination with N-(methyl toluyl)-methyl piperidines defined according to the structure:

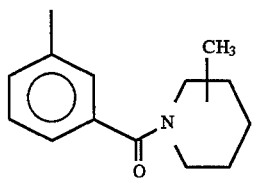

as described in U.S. Pat. No. 3,463,855 issued on Aug. 26, 1969, the specification for which is incorporated by reference herein. The compounds defined according to the structure:

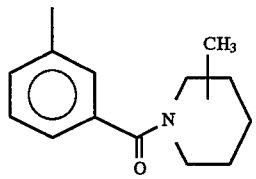

include:
N-(meta-toluyl)-2-methylpiperidine;
N-(meta-toluyl)-3-methylpiperidine; and
N-(meta-toluyl)-4-methylpiperidine.

The proportions of compounds defined according to the structure:

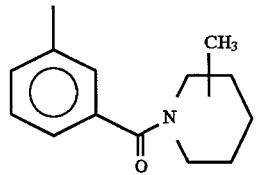

to the geraniol-containing composition described, supra, are between about 1 part N-(meta-toluyl) methylpiperidine:99 parts geraniol-containing composition of our invention down to 99 parts geraniol-containing composition of our invention:1 part N-(meta-toluyl)-methylpiperidines.

In addition, the compositions useful in repelling insects of our invention can also contain 1-nonen-3-ol described and claimed in U.S. Pat. Nos. 4,693,890 and 4,759,228 issued on Jul. 26, 1988, the specifications for which are incorporated by reference herein. The ratio of 1-nonen-3-ol:geraniol-containing composition of our invention useful in repellent compositions may vary from about 1 part 1-nonen-3-ol:99 parts geraniol-containing composition of our invention down to 99 parts 1-nonen-3-ol:1 part geraniol-containing composition of our invention.

In addition to the soap fabrication, another aspect of our invention relates to the formation of repelling articles containing the geraniol-containing compositions of our invention, that is, articles useful for repelling house flies (*Musca domestica* L.(Diptera:Muscidae)) or mosquitoes (*Aedes aegyptae*) in combination with compatible polymers which may or may not be biodegradable (for example, high density polyethylene or low density polyethylene, or biodegradable polymers such as biodegradable thermoplastic polyurethanes as disclosed in Japan Kokki Tokyo Koho 92/13710 (abstracted at Chem. Abstracts Volume 116:236374q), biodegradable ethylene polymers having ester linkages in the main chain such as that disclosed by Japan Kokki Tokyo Koho 92/50224 (abstracted at Chem. Abstracts Volume 116:236397z), biodegradable ethylene polymers disclosed by Japan Kokki Tokyo Koho 92/50225 (abstracted at Chem. Abstracts Volume 116:126398a) and poly(epsilon caprolactone) homopolymers and compositions containing same as disclosed in U.S. Pat. Nos. 4,496,467; 4,469,613 and 4,548,764 the specifications for which are incorporated herein by reference). Thus, another aspect of our invention provides a process for forming geraniol composition containing polymeric particles such as foamed polymeric pellets which include a relatively high concentration of the geraniol-containing composition of our invention as defined, supra.

Thus, another aspect of our invention relates to the formation of geraniol-containing composition polymeric pellets by means of introduction into a single or twin screw extruder, in series, a thermoplastic polymer followed by the geraniol-containing composition of our invention which is compatible with the thermoplastic polymer, in turn, (optionally) followed by introduction of gaseous blowing agent or blowing agent which will produce a gas which is inert to the polymer and to the geraniol-containing composition previously introduced into the extruder.

The advantages of using a foamed polymeric particle are multiple, to wit:
improved handling;
greater retention of the geraniol-containing composition when not in use;
greater length of time during which the release of the geraniol-containing composition of our invention from the polymer is at "steady state" or "0 order".

The nature of the extruder utilized in the process of our invention to form the geraniol-containing composition-containing polymer particles of our invention may be either single screw or double screw. Thus, the types of extruder that can be used are disclosed at pages 246–267 and 332–349 of the Modern Plastics Encylopedia, 1982-1983, published by the McGraw-Hill Publishing Company, the disclosure of which is incorporated by reference herein. More specifically, examples of extruders which are useable in carrying out one of the processes of our invention (with modification for introduction of the geraniol-containing compositions of our invention) downstream from the introduction of the polymer and with further modification that the gaseous blowing agent is introduced still further downstream from the point of introduction of the geraniol-containing composition of our invention are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling model 4000 and 5000 series extruder manufactured by Sterling Extruder Corporation of 901 Durham Avenue, South Plainfield, N.J.;

4. CRT ("Counter-Rotating Tangential"), Twin Screw Extruder manufactured by Welding Engineers, Inc. of King of Prussia, Pa. 19406;

5. The Leistritz Twin Screw Dispersion Compounder manufactured by the American Leistritz Extruder Corporation of 198 U.S. Route 206 South, Somerville, N.J. 08876;

6. The ZSK Twin Screw Co-Rotating Extruder manufactured by the Werner & Pfleiderer Corporation of 663 East Crescent Avenue, Ramsey, N.J. 07446;

7. The Farrel Extruder manufactured by Farrel Connecticut Division, Emhart Machinery Group, Ansonia, Conn. 06401;

8. The MPC/V Baker Perkins Twin Screw Extruder manufactured by the Baker Perkins Inc. Chemical Machinery Division of Saginaw, Mich. 48601; and 9. The Berstorff single screw, twin screw, or foam extrusion equipment manufactured by Berstorff Corporation, P.O. Box 240357, 8200-A Arrowing Blvd., Charlotte, N.C. 28224.

In producing the geraniol-containing composition-containing polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene/vinyl acetate with about 9 to 60% vinyl acetate and ethylene/ethyl acrylate with about 6 to 18% ethyl acrylate.

Resins of the type disclosed for use as co-polymers are commerically available in the molding powder form; for example, ethylene vinyl acetate co-polymers are marketed by the E. I. dupont Nemours Company under the tradename "ELVAX®" and by the Arco Polymer Division under the trademark "DYLAND®" and by the Exxon Corporation of Linden, New Jersey under the trademark "DEXXON®. Ethylene/ethyl acrylate co-polymers are marketed by Union Carbide Corporation under the trademark "EEA RESIN®.

The polymer is added to the single screw or twin screw extruder at a feed rate in the range of from about 80 up to about 300 pounds per hour while maintaining the temperature of the screw extruder between about 160° C. and about 240° C. If the polymer or co-polymer powder is added to the extruder at a reference "barrel segment", then the geraniol-containing composition of our invention is added to the extruder under pressure downstream from the retention point of the polymer at one or more of "barrel segments" (S-2, S-3, S-5, S-6, S-7, S-8 or S-9)(referring to FIG. 9 briefly described, supra, and described in detail, infra).

The proportion of geraniol-containing composition (taken further together with other insect repelling materials, if desired) to resin can vary from small but effective amounts on the order of about 1% of the weight of the resin body up about 45% by weight of the resin body. In general, it is preferred to use between about 5% up to about 30% based on the weight of the resin body of insect repellent composition of our invention. This is an optimum amount balancing the proportion of the insect repellent composition of our invention against the time period over which the article emits the insect repellent composition and against the tendency of the components of the insect repellent composition to oil out either individually or in combination. This "oiling out" is specifically avoided as a result of the use of the foaming agent discussed, infra.

Various polymers are useful in the practice of our invention. Specific examples of polymers useful in the practice of our invention are as follows:

(a) DYLAN® brand of low density polyethylene DYLAN® is a trademark owned by the Atlantic Richfield Company of Los Angeles, Calif.;

(b) DYLITE® of expandable polystyrene composition, DYLITE® is a trademark of Atlantic Richfield Company of Los Angeles, Calif.;

(c) SUPER DYLAN® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/alpha-olefin as exemplified and disclosed in U.S. Pat. No. 4,369,291, the specification for which is incorporated by reference herein;

(g) Poly-alpha-olefins as exemplified in Canadian Letters Pat. No. 1,137,069 issued on Dec. 7, 1982, the specification for which is incorporated by reference herein;

(h) Polymeric compositions as disclosed in Canadian Letters Patent No. 1,137,068 issued on Dec. 7, 1982, the specification for which is incorporated by reference herein;

(i) Poly-alpha-olefins disclosed in Canadian Letters Patent No. 1,137,067, the specification for which is incorporated by reference herein;

(j) Polyolefins described in Canadian Letters Patent No. 1,137,066, the specification for which is incorporated by reference herein;

(k) Polyethylene oxides as disclosed in Canadian Letters Patent No. 1,137,065 issued on Dec. 7, 1982, the specification for which is incorporated by reference herein;

(l) Olefin polymers and co-polymers as disclosed in Canadian Letters Patent No. 1,139,737, the disclosure of which is incorporated by reference herein. Canadian Letters Patent No. 1,139,737 was issued on Jan. 18, 1983;

(m) Polyolefins disclosed in Canadian Letters Patent No. 1,139,738, the disclosure of which is incorporated by reference herein. Canadian Letters Patent No. 1,139,738 was issued on Jan. 18, 1983;

(n) Chlorinated PVC as disclosed in Polymer 1982, 23 (7,Suppl.), 1051-6 abstracted at Chem. Abstracts Volume 97:14550y, 1982;

(o) Polyepsilon caprolactone co-polymers made by means of alcohol initiated polymerization as disclosed in J. Polym. Sci. Polym. Chem. Ed. 1982, 20(2), pages 319-26, abstracted at Chem. Abstracts, Volume 96:123625x, 1982;

(p) Styrene acrylonitrile co-polymers as disclosed in Diss. Abstracts Int. B, 1982, 42(8), 3346 and abstracted at Chem. Abstractss Volume 96:143770n, (1982);

(q) Co-polymers of epsilon caprolactone with 1,4-butane diol as disclosed at Kauch Rezine, 1982, (2), 8–9, abstracted at Chem. Abstracts Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al, J. Polym. Sci. Plym. Ed. 1982, 20(2), 191–203;

(t) Plasticized polyepsilon caprolactone co-polymers containing dimethyl phthalate plasticizers as set forth in Japanese Patent No. J81/147844, abstracted at Chem. Abstracts Volume 96:69984y (1982), the specification for which is incorporated by reference herein;

(u) Maleic anhydride modified adducts of polyepsilson caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Examples of poly(epsilon caprolactone) homopolymers as set forth, for example, in U.S. Pat. No. 4,496,467 are those having the structures:

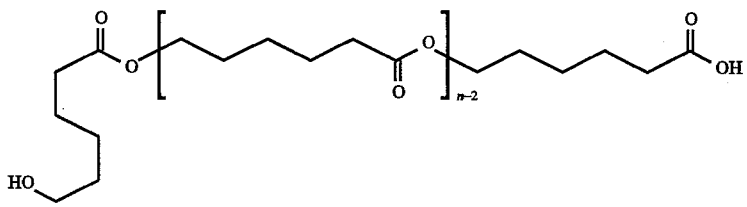

and

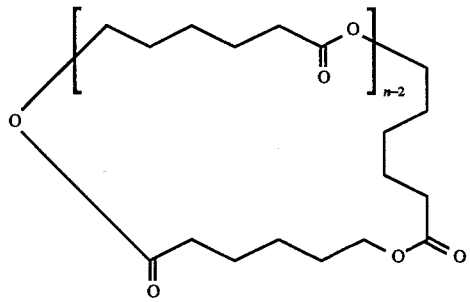

wherein n represents an integer of from about 500 up to about 1200 with the proviso that the average "n" varies from about 600 up to about 800.

Downstream from the addition point of the geraniol-containing composition of our invention taken alone or taken together with other insect repellent agents and fragrance materials, optionally, the gaseous or liquid containing blowing agent may be added (e.g., at "barrel segments" (S-5, S-6, S-7, S-8, S-9 or S-10) using the polymer addition "barrel segment" as a refrence "barrel segment" S-1. Examples of the gaseous blowing agents are carbon dioxide, nitrogen, mixtures of nitrogen and carbon dioxide in proportions of from 1 up to 99% by volume nitrogen and from 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 to about 150 psig. Higher pressures may be used without adversely affecting the usefulness of the foamed insect repellent composition-containing particle.

The feed rate range of insect repellent composition-containing but not limited to the geraniol-containing compositions of our invention, may be between about 0.5% up to about 45% by weight of the polymer.

The dies of the extruder may create rod, sheet, film or ribbon. The resulting product may then, if desired, be pelletized to form insect repellent composition-containing polymer particles or the ribbon may be used "as is" as an insect repellent-containing polymeric article of manufacture itself.

In addition to the optional gaseous blowing agents (which are necessarily "inert" gases), blowing agents may be added at the same point on the extruder which will create gaseous voids in the insect repellent-containing polymer articles of our invention and these "blowing agents" are well known to one having ordinary skill in the art. Examples of such non-gaseous containing materials which yield gases on admixture with the polymer in the extruder but which are still insert to the insect repellent (or attractant as the case may be) are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, line 1–5, the specification for which is incorporated by reference herein;

(iii) Dichlorotetrafluoromethane, tetramethylmethane, monochlorodifluoromethane, dichlorodifluoromethane, and dichlorotetrafluoromethane as described in U.S. Pat. Nos. 2,948,664 and 2,948,665 issued on Aug. 9, 1990, the specification for which is incorporated by reference herein; and (iv) Azo bis(formamide), diazoaminobenzene: N,N-dinitrosopentamethylene tetramine; N,N-dimethyl, N,N-dinitrosoterephthalamide; p,p'-oxy-bia(-benzen sulfonyl semicarbazide); aza bis-(isobutyronitrile) p,p'-oxy-bis(benzene sulfonyl hydrazide); p,p'-diphenyl-bis (sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and, if desired, pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

In addition, our invention relates to candle body materials which on use are both insect repellent and perfuming which contain the geraniol-containing composition of our invention and, if desired, other insect repellent materials including, for example, at least one of the compounds having the structure:

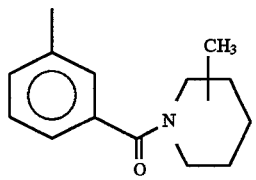

in order to repel house flies (*Musca domesfica L.*(Diptera:Muscidae)) and/or mosquitoes (*Aedes aegyptae*).

The house fly and mosquito-repellent-perfuming compositions which form part of the candle body materials are within the following specifications:

(I) from 5 up to 100% by weight of an efficacious perfuming/insect repellent composition containing the geraniol-containing composition of our invention; and (II) from 0 up to 95% by weight of a standard perfuming substance (non-insect repellent or insect repellent) which may include but is not limited to:
1-nonen-3-ol;
1-octen-4-ol;
alpha-damascone;
beta-damascone;
delta-damascone;
trans,trans delta-damascone;
methyl jasmonate;
dihydromethyl jasmonate;
the schiff base of vanillin and methyl anthranilate;
the schiff base of ethyl vanillin and methyl anthranilate;
vanillin; and
ethyl vanillin.

The foregoing formula may require a solubilizing agent, e.g., the methyl ester of dihydroabietic acid (commerical name: HERCOLYN D®), benzyl benzoate, isopropyl myristate and/or $C_{12}$-$C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;

(ii) an alkanol amide or alkanol amine; and (iii) a stearic acid compound.

The weight ratio of candle body:insect repellent/ perfumant substance or our invention may vary from about 0.8% up to about 10% with a range of from about 0.8% up to about 2.0% being preferred when no non-insect repelling perfume oil is used in conjunction with the geraniol-containing composition of our invention; and with a range of from about 1.5% up to about 10% by weight of the overall composition being preferred when a non-insect repelling perfume oil is used in conjunction with the geraniol-containing composition of our invention.

Specifically, the polyamide may be a "VERSAMID®" resin which is a thermoplastic condensation product of polymerized linoleic acid with various polyamine compounds such as ethylene diamine, ethylene triamine and the like. Specific "VERSAMID®" compounds are "VERSAMID®900", "VERSAMID®930", "VERSAMID®940", "VERSAMID®948", "VERSAMID®950" and "VERSAMID®1635". These compounds are products of the Henkel Chemical Corporation of Minneapolis, Minn.

Another substance required in the clear candle composition consists of about 20–55% by weight of an alkanol amine or alkanol amide prepared by the reaction of a fatty acide ester and amine whereby the ester and the amine are in substantially equal proportions, for example, compounds such as BARLOL®12C2 (manufactured by the Baroid Chemical Company) a monoalkyl diethanolamine having 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready incorporation of the insect repellent/ perfumant compositions of our invention up to a level of approximately 5% (total proportion of perfume oil-insect repellent composition). They are carriers for the perfumant/ insect repellent and may be used in a proportion of between 1 and 50% by weight of the composition although the preferable range is between 20 to 30%. In this connection it is possible to use up to about 10% by weight of a perfumant/ insect repellent if part of the formula is replaced by the material "NEVEX®100", a product which is a coumarin-indene copolymer resin of very little unsaturation manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperature. Such a gel is disclosed in U.S. Pat. No. 3,645,705 issued on Feb. 29, 1972, the disclosure of which is incorporated by reference herein. Such compositions of matter include:

(a) from about 35% up to about 85% by weight of an oil which is normally liquid at room temperature chosen from the group consisting of light mineral oils and natural oils having iodine values substantially within the range of 40–135;

(b) from about 7% up to about 40% by weight of a long chain polyamide having a molecular weight substantially within the range of 6000–9000 and a softening point substantially within the range of 18° C.–48° C.; and (c) from about 7% up to about 30% of an alcohol selected from the group consisting of 8 to 12 carbon primary alcohols.

Similarly, when used in insect traps, the attractants of our composition can be used in the same polymers as the repellents. Thus, for example, our invention contemplates one or a combination of the attractants (at a level of from about 1% up to about 45% by weight of the polymer composition):

lavender absolute;
benzoin having the structure:

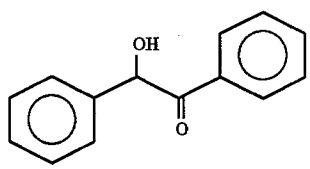

dimethyl benzyl carbinyl acetate having the structure:

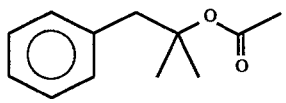

jasmine absolute;
racemic borneol having the structure:

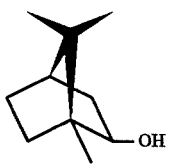

d-limonene having the structure:

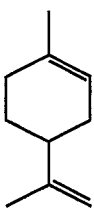

dihydro linalool having the structure:

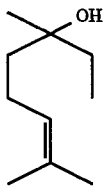

imbedded in the interstices of a microporous polymer which may be one of the polymers as set forth, supra.

Furthermore, the insect attractant-containing polymers of our invention may be insect attractant-containing biodegradable polymers as set forth, supra.

DETAILED DESCRIPTION OF THE DRAWINGS

The data set forth in FIGS. 1, 2, 3, 4, 5A, 5B, 5C, 6A, 6B, 7A, 7B, 8A and 8B were determined using the olfactometer of FIG. 10 and the insect trap of FIG. 21. Referring to the olfactometer of FIG. 10, said olfactometer is described in detail in U.S. Pat. No. 5,118,711 issued on Jun. 2, 1992, the specification for which is incorporated by reference herein.

Referring to FIG. 10, air supply source 3634 provides air to mixing station 3636 wherein the air is mixed with treatment agent from treatment agent source 3635 (source of, for example, the repellent a 50–100% geraniol-containing composition or the attractant, lavender absolute). The resulting mixture passes through tube 3636g and enters the apparatus through the side portals. The entry is through a spacer plate and above base plate 3625. The entry of the air-treatment agent is in a direction parallel to the surface of base plate 3625. Thus, the base plate 3625 is separated from spacer plate 3629 for the air-treatment agent (e.g., the geraniol-containing composition of our invention).

Air exits through line 3633a using exhaust fan 3633. The air exit is indicated by reference numeral 3537.

Simultaneously, with the supplying of air and treatment agent from mixing station 3636, light is supplied from beneath the enclosed insect feeding and/or stimulating means through light guides 3652, from light source 3551 which is powered by the electric power supply 3550 marketed by RADIO SHACK® Division of Tandy Corporation of Fort Worth, Tex. 76102 under the trademark ARCHER®, Catalog No. 276-228 ("1.0 mm optical plastic fiber length 5 meter"). An example of light source 3551 is KRATOS Monochromatic Illuminator GM 100 Miniature VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator. The base plate 3625 is also separated from the spacer plate 3629 for the light guides 3652 whereby the light guides 3652 are held in place in the base plate 3625 whereby the light (or other forms of radiation) is directed in a direction perpendicular to the electrical sensor element 3610. Air supply source from location 3634 and treatment agent from location 3635 is mixed at mixing station 3636 whereupon treatment agent and air in admixture is passed through lines 3636a and 3636g through portals located in the spacer element 3628 in a direction along a directional vector parallel to the electrical sensing element 3610 held in place by holders 3610a and 3610b. The electrical sensing elements are located directly below the horizontally positioned insect feeding and/or stimulating microporous substantially planar lamina 3670 which is held in place by ring 3660 located on spacer plate 3629 spaced from the base plate 3625 by spacer ring 3628. It should be noted that the spacer plate 3629, spacer ring 3628 and base plate 3625 enclose the entire "enclosed insect feeding and/or stimulating means" which have controlled limited access to the external environment surrounding the apparatus and in which the insects to be tested, e.g., mosquitoes or house flies are placed.

The insect attractant quantitative detecting means made up of wires 3699 (the entire grid being denoted using reference numeral 3610) is located immediately beneath the porous membrane 3670, the outer surface of which contains a feeding stimulant composition or stimulant composition for insects (for example, agar). Immersed in the feeding stimulate composition or stimulant composition for insects (e.g., agar) is electrode 3679 connected to wire 3619 which connects with either wire 3619a or 3619b which is connected to the grid wires 3699 (which make up the insect attractant quantitative detecting means located immediately below lamina 3670).

As stated, supra, the sensor causes an electrical impulse caused by the pressure of the insects landing to proceed through wires 3619a and 3619b to an electrically biased differential amplifier 3639 (using electrical power supply 3539) also connected to wire 3619c which is connected to the electrode 3679 which is immersed in the feeding stimulant composition or stimulant for the insect and then to a multi-channel A.C. converter 3523. Converter 3523 is associated with program tape storage 3524, printer 3520 and data link to digital computer 3521. Differential amplifier 3639 is connected in series to electrical bias for psuedo host 3669 which in turn is connected to wire 3619 which in turn is connected to the electrode 3679 immersed in the insect stimulant composition located on the surface of porous lamina 3670.

Referring to the testing apparatus, the semiochemical field trap 1000 for blood feeding arthropods, field trap 1000 is located in a three-space with axes perpendicular to one another. The semiochemical field trap 1000 is shown in perspective view in FIG. 21 comprising:

(1) an upright vertically disposed housing;

(2) extending outwardly from the housing a plurality of horizontally disposed hollow housings 116a and 116b which have contained therein insect sticky traps;

(3) air 138 and/or carbon dioxide supply means 134, 136 for supplying air and/or carbon dioxide into the vertical hollow housing and then through the plurality of horizontally disposed hollow housings 116a and 116b; and (4) at least one power supply means for energizing radiation means located on the vertical hollow housing whereby on engagement of the power supply means with the radiation means and operation of the air 138 and/or carbon dioxide supply means 134, 136, arthropods in the vicinity of the trap are attracted by the activated radiation means and the gas emanating from the horizontally disposed hollow housing 116a to a location so close to the trap 1000 that in the event that an attracting semiochemical located in the housings 116a and 116b is detected by at least one of the arthropods, at least one of the arthropods will enter the inner void of the horizontally disposed hollow housings 116a and 116b counter current the gas stream emanating therefrom and remain permanently entrapped therein.

The semiochemical field trap 1000 of FIG. 21 is disclosed in detail in application for U.S. patent, Ser. No. 887,138 filed on May 22, 1992, which is now U.S. Pat. No. 5,228,233, the specification for which is incorporated by reference herein.

FIG. 1 is a series of graphs depicted in three-dimensions (in a rectangular mode for the "X" and "Y" axes) showing the relative attractiveness or repellency of air, lavender absolute and a mixture containing 61.49 mole percent geraniol, 13.98 mole percent nerol and 24.53 mole percent citronellol with respect to attractiveness or repellency of Aedes aegyptae. The graph indicated by reference numeral 101 is for air. The graph indicated by reference numeral 103 is for lavender absolute. The graph indicated by reference numeral 105 is for the mixture containing 61.49 mole percent geraniol, 13.98 mole percent nerol and 24.53 mole percent citronellol. The "X" axis along which the particular materials are measured insofar as their attractiveness or repellency is concerned is indicated by reference numeral 107. The number of insects collected per interval is indicated on the "Y" axis and the "Y" axis is indicated by reference numeral 100. The results are tabulated in Table I as follows:

TABLE I

| Composition Tested | Graph No. | Insects Collected per Interval | | | | | | |
|---|---|---|---|---|---|---|---|---|
| Geraniol/Nerol/Citronellol Mixture | 105 | 0 | 3 | 1 | 0 | 0 | 0 | 0 |
| Air | 101 | 0 | 34 | 62 | 47 | 38 | 160 | 70 |
| Lavender Absolute | 103 | 0 | 2 | 92 | 211 | 13 | 0 | 1 |

FIG. 2 is a series of graphs depicted in three-dimensions (in a rectangular mode for the "X" and "Y" axes) showing the relative attractiveness or repellency of benzoin and a mixture containing 61.49 mole percent geraniol, 13.98 mole percent nerol and 24.53 mole percent citronellol with reference to attractiveness or repellency for Aedes aegyptae. The graph indicated by reference numeral 201 is the graph for the mixture of geraniol, nerol and citronellol. The graph indicated by reference numeral 203 is the graph for benzoin. The results are tabulated in Table II, as follows:

TABLE II

| Composition Tested | Graph No. | Insects Collected per Interval | | | | | | |
|---|---|---|---|---|---|---|---|---|
| Benzoin | 203 | 0 | 88 | 445 | 501 | 92 | 166 | 304 |
| Mixture of Geraniol, Nerol and Citronellol | 201 | 0 | 10 | 29 | 13 | 21 | 37 | 9 |

FIG. 3 is a series of graphs depicted in three-dimensions (in a rectangular mode for the "X" and "Y" axes) showing the relative attractiveness or repellency of the materials:
Tridecene nitrile;
Air;
Jasmine absolute;
Dimethyl benzyl carbinyl acetate;
Mixture of 81.28% mole percent geraniol and 18.72 mole percent mixture of nerol and citronellol (mole ratio of citronellol:nerol being 1.78).
The test data is for Musca domestica L.(Diptera:Muscidae) (the house fly). The graph indicated by reference numeral 307 is the graph for the geraniol-nerol-citronellol mixture. The graph indicated by reference numeral 305 is for the dimethyl benzyl carbinyl acetate. The graph indicated by reference numeral 303 is for jasmine absolute. The graph indicated by reference numeral 302 is for air. The graph indicated by reference numeral 300 is for tridecene nitrile. The results are tabulated in Table III as follows:

TABLE III

| Composition Tested | Graph No. | Insects Collected per Interval | | | | | | |
|---|---|---|---|---|---|---|---|---|
| Mixture of Geraniol, Nerol and Citronellol | 307 | 0 | 2 | 16 | 4 | 10 | 0 | 4 |
| Dimethyl benzyl carbinyl acetate | 305 | 0 | 44 | 20 | 14 | 58 | 13 | 15 |
| Jasmine absolute | 303 | 0 | 16 | 187 | 23 | 16 | 23 | 16 |
| Air | 302 | 0 | 4 | 11 | 5 | 5 | 5 | 385 |
| Tridecene nitrile | | 0 | 10 | 23 | 8 | 1 | 10 | 2 |

FIG. 4 is a series of graphs depicted in three-dimensions (in a rectangular mode for the "X" and "Y" axes) showing the relative attractiveness or repellency of air and a mixture of 61.49 mole percent geraniol, 13.98 mole percent nerol and 24.53 mole percent citronellol. The data is with respect to attractancy or repellency against Aedes aegyptae. The graph indicated by reference numeral 401 is for air. The graph indicated by reference numeral 400 is for the geraniol-nerol-citronellol mixture. The results are tabulated in Table IV as follows:

TABLE IV

| Composition Tested | Graph No. | Insects Collected per Two Hr. Interval | | | | | | |
|---|---|---|---|---|---|---|---|---|
| Geraniol-Nerol-Citronellol Mixture | 400 | 0 | 4 | 1 | 4 | 4 | 2 | 20 |
| Air | 401 | 0 | 157 | 148 | 293 | 278 | 246 | 329 |

FIGS. 5A, 5B and 5C are series of graphs depicted in three-dimensions (in a rectangular mode for the "X" and "Y" axes) showing the relative attractiveness and repellency of air, d-limonene, a mixture containing 61.49 mole percent geraniol, 13.98 mole percent nerol and 24.53 mole percent citronellol, and borneol (racemic). The graphs indicated by reference numerals 502a, 502b and 502c respectively on FIGS. 5a, 5b and 5c are for d-limonene. The graphs indicated by reference numerals 501a, 501b and 501c are for the geraniol-nerol-citronellol mixtures. The graphs indicated by reference numerals 500a, 500b and 500c are for borneol (racemic). The graphs indicated by reference numerals 503b and 503c are for air. The results are tabulated in Tables V(A), V(B) and V(C) as follows:

TABLE V(A)

| Composition Tested | Graph No. | Insects Collected Per Interval (10 minute Intervals Totalling one Hour) | | | | | | |
|---|---|---|---|---|---|---|---|---|
| D-limonene | 502a | 0 | 26 | 324 | 102 | 510 | 146 | 5 |
| Geraniol-Nerol-Citronellol Mixture | 501a | 0 | 0 | 0 | 0 | 0 | 0 | 0 |
| Borneol (Racemic) | 500a | 0 | 133 | 87 | 238 | 167 | 232 | 191 |

Data for *Aedes aegyptae*.

TABLE V(B)

| Composition Tested | Graph No. | Insects Collected Per Interval (One Hour Intervals Totalling Six Hours) | | | | | | |
|---|---|---|---|---|---|---|---|---|
| D-limonene | 502c | 0 | 5 | 113 | 155 | 117 | 167 | 128 |
| Air | 503b | 0 | 4 | 34 | 46 | 116 | 156 | 184 |
| Mixture of Geraniol, Nerol and Citronellol | 501b | 0 | 0 | 0 | 0 | 0 | 0 | 0 |
| Borneol (Racemic) | 500b | 0 | 191 | 165 | 184 | 214 | 171 | 233 |

Insects tested for: *Aedes aegyptae*.

TABLE V(C)

| Composition Tested | Graph No. | Insects Collected Per Interval (Two Hour Intervals Totalling Twelve Hours) | | | | | | |
|---|---|---|---|---|---|---|---|---|
| D-limonene | 502c | 0 | 128 | 130 | 169 | 70 | 109 | 128 |
| Air | 503c | 0 | 184 | 73 | 91 | 93 | 80 | 34 |
| Mixture of Geraniol, Nerol and Citronellol | 501c | 0 | 0 | 2 | 8 | 6 | 1 | 1 |
| Borneol (Racemic) | 500c | 0 | 233 | 247 | 155 | 175 | 139 | 202 |

Insects Tested For: *Aedes aegyptae*.

FIGS. 6A and 6B are series of graphs depicted in three-dimensions (in a rectangular mode for the "X" and "Y" axes) showing the relative attractiveness and repellency for *Aedes aegyptae* of air and a mixture containing 61.49 mole percent geraniol, 13.98 mole percent nerol and 24.53 mole percent citronellol. The graphs indicated by reference numerals 603a and 603b are for air. The graphs indicated by reference numerals 601a and 601b are for the geraniol-nerol-citronellol mixtures. The results are tabulated in Tables VI(A) and VI(B) as follows:

TABLE VI(A)

| Composition Tested | Graph No. | Insects Collected Per Interval Ten Minute Intervals Totalling One Hour) | | | | | | |
|---|---|---|---|---|---|---|---|---|
| Air | 603a | 0 | 230 | 382 | 381 | 268 | 374 | 456 |
| Geraniol-Nerol-Citronellol Composition | 601a | 0 | 5 | 0 | 0 | 0 | 0 | 0 |

TABLE VI(B)

| Composition Tested | Graph No. | Insects Collected Per Interval (One Hour Intervals Totalling Six Hours) | | | | | | |
|---|---|---|---|---|---|---|---|---|
| Air | 603b | 0 | 456 | 269 | 246 | 371 | 316 | 287 |
| Geraniol-Nerol-Citronellol Composition | 601a | 0 | 0 | 0 | 0 | 3 | 2 | 0 |

FIGS. 7A and 7B are series of graphs depicted in three-dimensions (in a rectangular mode for the "X" and "Y" axes) showing the relative attractiveness or repellency for *Aedes aegyptae* of the following materials: air and the mixture containing 61.49 mole percent geraniol, 13.98 mole percent nerol and 24.53 mole percent citronellol. The graphs indicated by reference numerals 703a and 703b are for air. The graphs indicated by reference numerals 701a and 701b are for the geraniol-nerol-citronellol mixture.

The results are tabulated in Tables VII(A) and VII(B) below:

TABLE VII(A)

| Composition Tested | Graph No. | Insects Collected Per Interval (Ten Minute Intervals Totalling One Hour) | | | | | | |
|---|---|---|---|---|---|---|---|---|
| Air | 703a | 0 | 84 | 404 | 303 | 24 | 323 | 550 |
| Geraniol-Nerol-Citronellol Composition | 701a | 0 | 0 | 0 | 0 | 1 | 1 | 0 |

TABLE VII(B)

| Composition Tested | Graph No. | Insects Collected Per Interval (One Hour Intervals Totalling Six Hours) | | | | | | |
|---|---|---|---|---|---|---|---|---|
| Air | 703b | 0 | 550 | 254 | 324 | 360 | 370 | 281 |
| Geraniol-Nerol-Citronellol Mixture | 701b | 0 | 0 | 0 | 0 | 0 | 0 | 0 |

FIGS. 8A and 8B are a series of graphs depicted in three-dimensions (in a rectangular mode for the "X" and "Y" axes) showing the relative attractiveness or repellency for *Aedes aegyptae* for the following materials: air, dihydrolinalool, TREO® (trademark of Primavera Products, Inc. of Northvale, N.J.) and benzaldehyde.

The graphs indicated by reference numerals 83a and 83b are for air. The graphs indicated by reference numerals 82a and 82b are for dihydrolinalool. The graphs indicated by reference numerals 81a and 81b are for TREO®. The graphs indicated by reference numerals 80a and 80b are for benzaldehyde. The results are tabulated in Tables VIII(A) and VIII(B) as follows:

TABLE VIII(A)

| Composition Tested | Graph No. | Insects Collected Per Interval (Ten Minute Intervals Totalling one Hour) | | | | | | |
|---|---|---|---|---|---|---|---|---|
| Air | 83a | 0 | 309 | 355 | 194 | 249 | 104 | 97 |
| Dihydrolinalool | 82a | 0 | 308 | 347 | 343 | 162 | 225 | 192 |
| TREO® | 81a | 0 | 372 | 332 | 463 | 317 | 314 | 231 |
| Benzaldehyde | 80a | 0 | 148 | 103 | 215 | 164 | 194 | 269 |

TABLE VIII(B)

| Composition Tested | Graph No. | Insects collected Per Interval (One Hour Intervals Totalling Six Hours) | | | | | | |
|---|---|---|---|---|---|---|---|---|
| Air | 83b | 0 | 218 | 161 | 200 | 194 | 158 | 233 |
| Dihydrolinalool | 82b | 0 | 263 | 332 | 290 | 228 | 312 | 287 |
| TREO® | 81b | 0 | 338 | 365 | 374 | 313 | 280 | 230 |
| Benzaldehyde | 80b | 0 | 182 | 152 | 78 | 103 | 48 | 184 |

FIG. 22 is the GC mass spectrum for the TREO® product tested as shown in Tables VIII(A) and VIII(B) and in FIGS. 8A and 8B. (Conditions: 50 meter×0.32 mm FS-OV-1 column programmed at 50°–225° C. at 2° C. per minute). The peak indicated by reference numeral 2117 is for cis-hexenyl acetate having the structure:

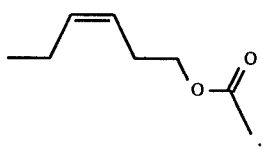

The peak indicated by reference numeral 2115 is the peak for d-limomene having the structure:

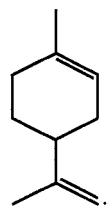

The peak indicated by reference numeral 2101 is for phenylethyl alcohol having the structure:

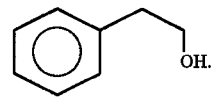

The peak indicated by reference numeral 2100 is for linalool having the structure:

The peak indicated by reference numeral 2116 is for benzyl acetate having the structure:

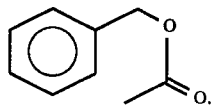

The peak indicated by reference numeral 2103 is for alpha-terpineol having the structure:

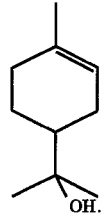

The peak indicated by reference numeral 2102 is for citronellol having the structure:

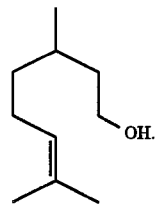

The peak indicated by reference numeral 2104 is for geraniol having the structure:

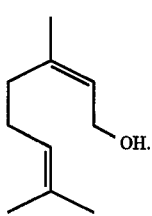

The peak indicated by reference numeral 2105 is for cyclamal having the structure:

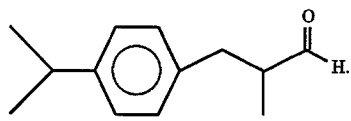

The peak indicated by reference numeral 2107 is for butylated hydroxy anisole having the structure:

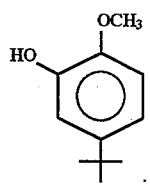

The peak indicated by reference numeral 2106 is the peak for lilial having the structure:

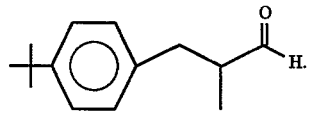

The peaks indicated by reference numerals 2110 and 2108 are for the TREO® base. The peak indicated by reference numeral 2112 is for UVINOL® M-40 having the structure:

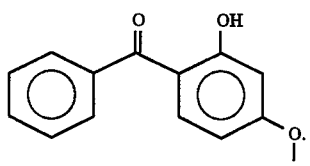

The peak indicated by reference numeral 2114 is for 4-methoxy-2-ethylhexyl cinnamate having the structure:

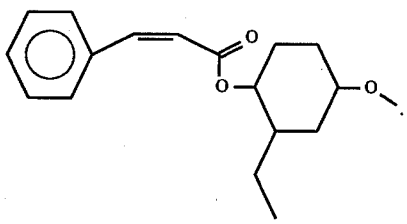

A preferred embodiment of our invention comprises an ellipsoidally-shaped detergent tablet 830 containing a solid plastic core 832 which can be fabricated from, for example, polyethylene, polypropylene, nylon, a biodegradable polymer such as poly(epsilon caprolactone) or any polymer capable of having therein microvoids from which an insect repelling substance, e.g., one of the geraniol-containing compositions of our invention will be controllably transported from the plastic core into and through the soap cake over a reasonable period of time during the use of the soap cake. Such polymers can be microporous polymers, such as those described in U.S. Pat. No. 4,247,498 issued on Jan. 27, 1981, the specification for which is incorporated herein by reference. Surrounding the central plastic core containing insect repellent 832, is detergent 830' which is in the solid phase at ambient conditions, e.g., room temperature and atmospheric pressure. Examples of workable detergents 830' are "elastic" detergents such as those described in U.S. Pat. No. 4,181,632 issued on Jan. 1, 1980, the disclosure of which is incorporated herein by reference, or "transparent" soaps such as those set forth in U.S. Pat. No. 4,165,293 issued on Aug. 21, 1979, the disclosure of which is incorporated herein by reference. Other examples of the detergent 830' useful in our invention are those set forth as "variegated soaps" in Canadian Letters Patent No. 1,101,165 issued on May 19, 1981.

On use of the soap tablet 830 or detergent bar, the insect repellent agent originally located in plastic core 832 is transported at a steady state from core 832 through core surface 831 through the detergent 830' and finally through the surface of the detergent bar at, for example, 833, 834, 835 and 836.

The detergent bar or tablet 830 of our invention may be of any geometric shape, for example, a rectangular parallelepiped tablet as is shown in FIGS. 15, 16 and 17 containing solid plastic core 839. The insect repellent located in solid plastic core 839 on use of the detergent bar passes through at steady state, surface 837 of FIG. 16, detergent 838 and finally surface 839 at, for example, locations 840, 841, 842 and 843. The environment surrounding the detergent bar on use thereof is then treated with the insect repellent at 843, 844 and 845, for example. Optionally, aromatizing agent can also be contained in the detergent bar (if desired) and so the environment surrounding the detergent bar on use thereof would also be aesthetically aromatized at 843, 844 and 845, for example if the geraniol-containing composition of our invention is insufficient for such aromatization. In certain instances such geraniol-containing compositions are indeed sufficient for such aromatization.

As is shown in FIGS. 18, 19 and 20 the plastic core of the detergent tablet 830 may have a single finite void at its center 851 (of FIGS. 19 and 20) in which the insect repellent agent and optionally any additional aromatizing agents are contained. The plastic core is a shell 848 having outer surface 852 (shown in FIGS. 19 and 20). The insect repellent agent (and optionally any additional aromatizing agent) contained in the void in the plastic core permeates through shell 848, past surfce 852 at a steady state, through the detergent 847 and to the environment at, for example, 856, 857 858 and 859.

In addition to the insect repellent contained in the core, e.g., core 839 or core void the core can also contain other materials for therapeutic use, for example, bacteriastats, deodorizing agents and the like which are compatible with the geraniol-containing compositions of our invention. In the alternative, the plastic core of the detergent tablet of FIGS. 18, 19 and 20 may have an empty single finite void at its center 851 with the insect repellent contained in the shell 848.

At the end of the use of the detergent tablet, the hollow core or the solid core can be used as an insect imparting and aroma imparting or air freshener household article. In addition, depending on the ratio of the volume of the void 851, to the solid part of the detergent table of FIGS. 18, 19 and 20, the detergent tablet of FIGS. 18, 19 and 20 can be so fabricated that it will float on the surface of the liquid in which it is being used and this physical attribute has certain obvious advantages.

FIG. 23 is a series of graphs depicted in three-dimensions (in a rectangular mode for the "X" and "Y" axes) showing the relative attractiveness or repellency of various compositions of matter for mosquitoes (Aedes aegyptae).

The graphs are based on experiments run for a total of one hour with six intervals of ten minutes each. The peak indicated by reference numeral 2305 is for air. The peak indicated by reference numeral 2307 is for the mixture containing 61.54 mole percent geraniol, 24.5 mole percent citronellol and 13.98 mole percent nerol.

The graph indicated by reference numeral 2303 is for the mixture containing 98.95 mole percent geraniol and 1.05 mole percent nerol.

The graph indicated by reference numeral 2301 is for the mixture containing 81.8 mole percent geraniol, 11.66 mole percent citronellol and 6.53 mole percent nerol. Table X(A) below sets forth the results in tabulated form:

TABLE IX(A)

| Composition Tested | Graph No. | Insects Collected Per Interval (Ten Minute Intervals Totalling One Hour) | | | | | | |
|---|---|---|---|---|---|---|---|---|
| Air | 2305 | 0 | 1 | 34 | 1 | 8 | 2 | 0 |
| Mixture of 61.54 mole percent geraniol, 24.5 mole percent citronellol and 13.98 mole percent nerol. | 2307 | 0 | 4 | 0 | 0 | 0 | 0 | 0 |
| Mixture 98.95 mole percent geraniol and 1.05 mole percent nerol. | 2303 | 0 | 2 | 0 | 0 | 0 | 0 | 0 |
| Mixture of 81.8 mole percent geraniol, 11.66 mole percent citronellol and 6.53 mole percent nerol. | 2301 | 0 | 5 | 0 | 0 | 0 | 1 | 0 |

FIG. 24 is a series of graphs depicted in three-dimensions (in a rectangular mode for the "X" and "Y" axes) showing the relative attractiveness or repellency of various compositions of matter for mosquiotes (Aedes aegyptae). The graphs are based on experiments run for a total of six hours with six intervals of one hour each. The results are tabulated in Table IX(B) below. The graph indicated by reference numeral 2405 is for air. The graph indicated by reference numeral 2407 is for a mixture of 61.54 mole percent geraniol, 24.5 mole percent citronellol and 13.98 mole percent nerol. The graph indicated by reference numeral 2403 is for a mixture of 98.95 mole percent geraniol and 1.05 mole percent nerol. The graph indicated by reference numeral 2401 is for a mixture of 81.8 mole percent geraniol, 11.66 mole percent citronellol and 6.53 mole percent nerol.

TABLE IX(B)

| Composition Tested | Graph No. | Insects Collected Per Interval (One Hour Each For A Total Of Six Hours) | | | | | | |
|---|---|---|---|---|---|---|---|---|
| Air | 2405 | 0 | 0 | 28 | 36 | 105 | 45 | 60 |
| Mixture containing 61.54 mole percent geraniol, 24.5 mole percent citronellol and 13.98 mole percent nerol. | 2407 | 0 | 0 | 0 | 0 | 0 | 0 | 0 |
| Mixture of 98.95 mole percent geraniol, and 1.05 mole percent nerol. | 2403 | 0 | 0 | 0 | 0 | 1 | 3 | 3 |
| Mixture of 81.8 mole percent geraniol, 11.66 mole percent citronellol and 6.53 mole percent nerol. | 2401 | 0 | 0 | 0 | 0 | 0 | 0 | 0 |

EXAMPLE I

The transparent candle base mixture is produced by intimately admixing the following ingredients:

| Ingredients | Parts by Weight |
|---|---|
| VERSAMID ® 1635 | 34.0 |
| Barlol 12C2 | 51.0 |
| Butyl Stearate | 3.5 |
| NEVEX ® 100 | 5.0 |
| SPAN ® | 1.5 |
| Isopropyl Isostearate | 4.0 |
| Isopropyl Myristate | 4.0 |

The foregoing mixture is placed in an autoclave and intimately admixed with a perfuming-insect repellent composition containing 95% by weight of geraniol and 5% by weight nerol of the total candle base composition.

The autoclave is sealed and heated to 180° C. under 15 atmospheres pressure and maintained with vigorous shaking for a period of five hours. At the end of the five hour period, the autoclave is depressurized (being under a nitrogen pressure atmosphere) and the autoclave is opened and the contents are then poured into cylindrical candle molds 4" in height and 2" in diameter containing 0.125" wicks. The resulting candles have efficacious mosquito and house fly repellencies and have aesthetically pleasing aromas on use.

The candles are effective in preventing house flies and mosquitoes from entering a room in which two candles have been burning for 15 minutes, the said room having dimensions of 6'×15'×15' and having a 3'×3' open portal adjacent to house fly and mosquito-infested region in the month of August, 1988 in the temperate zone of Highlands, N.J. adjacent Raritan Bay.

EXAMPLE II

A study was conducted to evaluate the efficacy of candles which are designated as "A", "B" and "C" in repelling house flies (*Musca domestica L.*(Diptera:Muscidae)).

Candle "A" contained 95% Paraffin Wax and 5% of 100% geraniol.

Candle "B" contained 90% Paraffin Wax and 10% citronellol oil.

Candle "C" contained only Paraffin Wax.

The candles are allowed to burn for 20 minutes and the number of house flies and mosquitoes repelled is recorded for the next 60 minutes with the following equipment and procedure:

Materials

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4-cm hole located in the center of each Masonite plate provided an escape for the test insects. A barrier was used to close the hole.

Attractant

A caged mouse was used as an attractant and was placed inside the chamber in the larger section of the repellency cage.

Test Insect

Adult House Flies (*Musca domestica L.*(Diptera:Muscidae)) are Test Insects.

Procedure

For each replicate, 75 to 100 adult house flies were removed from the rearing cage by means of a vacuum aspirator, and transferred by carbon dioxide anesthesia to the inner cage containing the mouse. The assembled cage was placed in one of the upper ventilation ports of the chamber. For each experimental situation the test insects were transferred to a clean cage containing the mouse. A house fly candle was placed centrally on the chamber floor and burned for 20 minutes before initiating the repellency counts. The maximum period for the repellency counts was 60 minutes. The first repellency count was made at 10 minutes after the burning ended, and subsequent counts were taken at 5-minute intervals thereafter. The number of house flies repelled were those escaping to the outside cage. For the control, counts were made in a similar manner, but no candle was burned.

The same three candles were used for all four replicates. Between replicates the chamber was exhausted, the Kraft paper flooring for the chamber was replaced, and the two screened repellency cages were submerged in hot detergent water, rinsed and dried.

Results

The overall average percent of house flies repelled for each candle for 60 minutes was as follows:

Candle "A"—94%

Candle "B"—53%

Candle "C"—16%.

What is claimed is:

1. A method of attracting *Aedes aegyptae* to an insect trap comprising the step of exposing the environment surrounding said trap to an insect attractant containing polymer which consists of a mixture of a polymer and from about 1% up to about 45% by weight of said polymer of d-limonene having the structure:

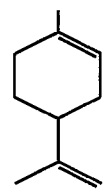

2. The method of claim 1 wherein the polymer is a biodegradable polymer.

3. The method of claim 2 wherein the biodegradable polymer is a polyepsilon caprolactone polymer or a polyurethane polymer.

* * * * *